(12) United States Patent
Etzel

(10) Patent No.: US 9,375,499 B2
(45) Date of Patent: Jun. 28, 2016

(54) ADSORPTIVE MEMBRANES FOR TRAPPING VIRUSES

(75) Inventor: Mark R. Etzel, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 2402 days.

(21) Appl. No.: 11/776,774

(22) Filed: Jul. 12, 2007

(65) Prior Publication Data

US 2008/0014625 A1 Jan. 17, 2008

Related U.S. Application Data

(60) Provisional application No. 60/830,917, filed on Jul. 14, 2006.

(51) Int. Cl.
| | |
|---|---|
| *C12Q 1/70* | (2006.01) |
| *A61L 2/00* | (2006.01) |
| *B01D 61/14* | (2006.01) |
| *B01D 67/00* | (2006.01) |
| *B01J 20/28* | (2006.01) |
| *B01J 20/32* | (2006.01) |
| *B01J 20/26* | (2006.01) |

(52) U.S. Cl.
CPC .............. *A61L 2/0017* (2013.01); *B01D 61/147* (2013.01); *B01D 67/0093* (2013.01); *B01J 20/261* (2013.01); *B01J 20/262* (2013.01); *B01J 20/2808* (2013.01); *B01J 20/28033* (2013.01); *B01J 20/321* (2013.01); *B01J 20/3212* (2013.01); *B01J 20/3219* (2013.01); *B01J 20/3248* (2013.01); *B01J 20/3251* (2013.01); *B01J 20/3253* (2013.01); *B01J 20/3255* (2013.01); *B01J 20/3285* (2013.01); *B01D 2325/12* (2013.01); *B01D 2325/16* (2013.01)

(58) Field of Classification Search
None
See application file for complete search history.

(56) References Cited

U.S. PATENT DOCUMENTS

| | | | |
|---|---|---|---|
| 3,743,722 | A | 7/1973 | Nolan |
| 3,834,990 | A | 9/1974 | Werle et al. |
| 3,856,715 | A | 12/1974 | Corte et al. |
| 4,066,506 | A | 1/1978 | Johnson et al. |
| 4,245,051 | A | 1/1981 | Reich et al. |

(Continued)

FOREIGN PATENT DOCUMENTS

| | | |
|---|---|---|
| EP | 0401005 | 12/1990 |
| EP | 0586268 | 3/1994 |

(Continued)

OTHER PUBLICATIONS

Johansson et al. Preparation and characterization of prototypes for multi-modal separation media aimed for capture of negatively charged biomolecules at high salt conditions. Journal of Chromatography A, 2003, vol. 1016, 21-33.*

(Continued)

*Primary Examiner* — Michelle S Horning
(74) *Attorney, Agent, or Firm* — Daniel A. Blasiole; Joseph T. Leone, Esq.; DeWitt Ross & Stevens SC

(57) ABSTRACT

A disposable, virus-trapping membrane, and a corresponding method to remove viruses from solution are described. The membrane includes a disposable, micro-porous filter membrane and a ligand immobilized on the membrane. The ligand irreversibly and selectively binds viruses. The ligand also has a pKa sufficiently high to repel antibodies via electrostatic charge repulsion.

**

(56) References Cited

U.S. PATENT DOCUMENTS

| | | |
|---|---|---|
| 4,452,916 A | 6/1984 | Boschetti |
| 4,981,497 A | 1/1991 | Hayes |
| 5,086,167 A | 2/1992 | Awad, Jr. |
| 5,110,914 A | 5/1992 | Awad, Jr. |
| 5,215,692 A | 6/1993 | Hörl |
| 5,259,936 A | 11/1993 | Ganzi |
| 5,344,560 A | 9/1994 | Sugo et al. |
| 5,354,472 A | 10/1994 | Voorhees et al. |
| 5,378,816 A | 1/1995 | Pungor et al. |
| 5,438,128 A | 8/1995 | Nieuwkerk |
| 5,543,054 A | 8/1996 | Charkoudian |
| 5,547,576 A | 8/1996 | Onishi et al. |
| 5,556,708 A | 9/1996 | Hörl |
| 5,567,615 A | 10/1996 | Degen |
| 5,627,217 A | 5/1997 | Rilling et al. |
| 5,659,071 A | 8/1997 | Nystrom et al. |
| 5,660,984 A | 8/1997 | Davis et al. |
| 5,667,775 A | 9/1997 | Holmes-Farley et al. |
| 5,783,087 A | 7/1998 | Vlock |
| 5,789,578 A | 8/1998 | Burton et al. |
| 5,817,716 A | 10/1998 | Le Perchec et al. |
| 5,834,596 A | 11/1998 | Ageland et al. |
| 5,854,384 A | 12/1998 | Kuroda et al. |
| 6,001,974 A | 12/1999 | Demmer |
| 6,033,719 A | 3/2000 | Keogh |
| 6,096,872 A | 8/2000 | Van Holten |
| 6,200,791 B1 | 3/2001 | Schwarz et al. |
| 6,281,252 B1 | 8/2001 | Holmes-Farley et al. |
| 6,294,090 B1 | 9/2001 | Nussbaumer |
| 6,294,163 B1 | 9/2001 | Dhal et al. |
| 6,365,395 B1 | 4/2002 | Antoniou |
| 6,534,639 B1 | 3/2003 | Manoharan et al. |
| 6,702,943 B1 | 3/2004 | Johansson et al. |
| 6,773,599 B1 | 8/2004 | Lowe et al. |
| 6,780,327 B1 | 8/2004 | Wu |
| 6,851,561 B2 | 2/2005 | Wu |
| 7,008,542 B2 | 3/2006 | Belew et al. |
| 7,041,216 B2 | 5/2006 | Dunkley |
| 7,060,776 B2 | 6/2006 | Algotsson et al. |
| 7,094,347 B2 | 8/2006 | Wu |
| 7,108,791 B2 | 9/2006 | Tkacik |
| 7,118,675 B2 | 10/2006 | Siwak |
| 7,160,464 B2 | 1/2007 | Lee et al. |
| 7,189,322 B2 | 3/2007 | Wu |
| 7,223,341 B2 | 5/2007 | Wu |
| 7,223,342 B2 | 5/2007 | Demmer |
| 7,264,958 B1 | 9/2007 | Koehl et al. |
| 7,279,094 B2 | 10/2007 | Hofmann |
| 7,294,743 B2 | 11/2007 | Algotsson et al. |
| 7,311,832 B2 | 12/2007 | Demmer |
| 7,316,919 B2 | 1/2008 | Childs et al. |
| 7,320,754 B2 | 1/2008 | Carlsson et al. |
| 7,326,776 B2 | 2/2008 | Boschetti |
| 7,396,465 B2 | 7/2008 | Wu |
| 7,465,397 B2 | 12/2008 | Siwak |
| 7,479,222 B2 | 1/2009 | DiLeo |
| 7,479,223 B2 | 1/2009 | DiLeo |
| 7,534,346 B2 | 5/2009 | Dunkley |
| 7,648,034 B2 | 1/2010 | Charkoudian |
| 7,655,793 B2 | 2/2010 | Herzer |
| 7,673,757 B2 | 3/2010 | Yavorsky |
| 7,678,269 B2 | 3/2010 | Cheng |
| 7,678,302 B2 | 3/2010 | Cheng |
| 7,700,743 B2 | 4/2010 | Angus |
| 7,807,054 B2 | 10/2010 | Dunkley |
| 7,824,548 B2 | 11/2010 | DiLeo |
| 7,846,682 B2 | 12/2010 | Bian |
| 7,867,784 B2 | 1/2011 | Engstrand |
| 2002/0025264 A1 | 2/2002 | Polizos et al. |
| 2002/0053252 A1 | 5/2002 | Duffy |
| 2002/0055094 A1 | 5/2002 | Reece et al. |
| 2002/0147282 A1 | 10/2002 | Mayes et al. |
| 2003/0133902 A1 | 7/2003 | Holmes-Farley et al. |
| 2003/0152548 A1 | 8/2003 | Mikos et al. |
| 2003/0162838 A1 | 8/2003 | Yumioka et al. |
| 2003/0171443 A1 | 9/2003 | Erbacher |
| 2003/0173220 A1 | 9/2003 | Bjellqvis et al. |
| 2003/0175966 A1 | 9/2003 | Wang et al. |
| 2003/0185788 A1 | 10/2003 | Rothbard et al. |
| 2003/0232969 A1 | 12/2003 | Lengsfeld et al. |
| 2003/0236323 A1 | 12/2003 | Ratner et al. |
| 2004/0078349 A1 | 4/2004 | Syrjala et al. |
| 2005/0040092 A1 | 2/2005 | Eilers et al. |
| 2005/0061543 A1 | 3/2005 | Sagayanathan et al. |
| 2005/0082483 A1 | 4/2005 | Oida et al. |
| 2006/0005457 A1 | 1/2006 | Harris et al. |
| 2006/0024264 A1 | 2/2006 | Kuroda et al. |
| 2006/0121217 A1 | 6/2006 | Childs et al. |
| 2006/0134595 A1 | 6/2006 | Rapp et al. |
| 2007/0106090 A1 | 5/2007 | Algotsson et al. |
| 2007/0151910 A1 | 7/2007 | Boschetti et al. |
| 2007/0154513 A1 | 7/2007 | Atanasoska et al. |
| 2007/0167613 A1 | 7/2007 | Johansson et al. |
| 2007/0193954 A1 | 8/2007 | Busson |
| 2007/0272607 A1 | 11/2007 | Kozlov et al. |
| 2008/0064861 A1 | 3/2008 | Sun |
| 2008/0076912 A1 | 3/2008 | Takkellapati et al. |
| 2008/0164211 A1 | 7/2008 | Lindner et al. |
| 2008/0193981 A1 | 8/2008 | Fahrner et al. |
| 2008/0207487 A1 | 8/2008 | DeFrees et al. |
| 2008/0210615 A1 | 9/2008 | Joehnck et al. |
| 2008/0264867 A1 | 10/2008 | Mika et al. |
| 2008/0275003 A1 | 11/2008 | Widmer et al. |
| 2008/0299671 A1 | 12/2008 | Glad et al. |
| 2008/0318300 A1 | 12/2008 | Koyama et al. |
| 2009/0050566 A1 | 2/2009 | Kozlov |
| 2010/0009867 A1 | 1/2010 | Carredano |

FOREIGN PATENT DOCUMENTS

| | | |
|---|---|---|
| EP | 0 494 848 B1 | 3/1997 |
| EP | 2 027 875 A1 | 2/2009 |
| FR | 2.014.613 | 4/1970 |
| JP | 58-89184 | 5/1983 |
| JP | 4-70904 | 3/1992 |
| JP | 07253423 A | 3/1995 |
| JP | 10-160719 | 6/1998 |
| WO | WO 2005/073711 A2 | 11/2005 |

OTHER PUBLICATIONS

Ahrer et al. Thermodynamic stability and formation of aggregates of human immunoglobulin G characterized by differential scanning calorimetry and dynamic light scattering. J Biochem Biophys Methods, Mar. 2006, vol. 66, 73-86.*

Phillips et al. Performance of a membrane adsorber for trace impurity removal in biotechnology manufacturing. Journal of Chromatography A, Jun. 2005, vol. 1078, 74-82.*

Bulletin 910. Guide to Solid Phase Extraction. p. 1-12. Copyrighted 1998 Sigma-Aldrich Co. No date available.*

Fujisawa et al. Assembly of bacteriophage phi X174: identification of a virion capsid precursor and proposal of a model for the functions of bacteriophage gene products during morphogenesis. J Virol. Oct. 1977;24(1):303-13.*

Anonymous. "Guidance for Industry: Q5A Viral Safety Evaluation of Biotechnology Products Derived from Cell Lines of Human or Animal Origin," International Conference on Harmonisation of Technical Requirements for Registration of Pharmaceuticals for Human Use (ICH), U.S. Department of Health and Human Services,1998.

Anonymous. "Guidance on Viral Safety Evaluation of Biotechnology Products Derived from Cell Lines of Human or Animal Origin." Fed. Regist. 1998, 63:51074-51084.

Anonymous. "Points to Consider in the Manufacture and Testing of Monoclonal Antibody Products for Human Use." Center for Biologics Evaluation and Research, Food and Drug Administration, U.S. Department of Health and Human Services, Rockville, MD, 1997.

Aranha-Creado et al. "Application of Bacteriophages as Surrogates for Mammalian Viruses: A Case for Use in Filter Validation Based on Precedents and Current Practices in Medical and Environmental Virology." PDA J. Pharm. Sci. Technol. 1999, 53:75-82.

(56) References Cited

OTHER PUBLICATIONS

Barsoum, J. "Concentration of Recombinant Baculovirus by Cation-Exchange Chromatography." BioTechniques, 1999, 26:834-840.
Benson et al. "Viral Evolution Revealed by Bacteriophage PRD1 and Human Adenovirus Coat Protein Structures." Cell 1999, 98, 825-833.
Boschetti, E. "Antibody Separation by Hydrophobic Charge Induction Chromatography." Trends Biotechnol. 2002, 20:333-337.
Brandt et al. "Membrane-based affinity technology for commercial scale purifications." Bio/Technology 1988, 6:779-782.
Brorson et al. "Bracketed Generic Inactivation of Rodent Retroviruses by Low pH Treatment for Monoclonal Antibodies and Recombinant Proteins." Biotechnol. Bioeng. 2003, 82:321-3293.
Brough et al. "Performance of a Novel Viresolve NFR Virus Filter." Biotechnol. Prog. 2002, 18:782-795.
Brument et al. "A Versatile and Scalable Two-Step Ion-Exchange Chromatography Process for the Purification of Recombinant Adeno-Associated Virus Serotypes-2 and -5." Molecular Therapy 2002, 6:678-686.
Charcosset, C. "Purification of proteins by membrane chromatography." J. Chem. Technol. Biotechnol 1998, 71:95-110.
Coetzee et al. "Properties of R Plasmid R772 and the Corresponding Pilus-Specific Phage PR772." J. Gen. Microbiol. 1979, 110:263-273.
Curtis et al. "Generic/Matrix Evaluation of SV40 Clearance by Anion Exchange Chromatography in Flow-Through Mode." Biotechnol. Bioeng. 2003, 84:179-186.
Das, R.C. "Progress and Prospects of Protein Therapeutics." American Biotechnology Laboratory 2003, 10:8-12.
Debelak et al. "Cation-Exchange High-Performance Liquid Chromatography of Recombinant Adeno-Associated Virus Type 2." J. Chromatogr. B 2000, 740:195-202.
DePalma, A. "Introducing Innovations to Downstream Process." Genetic Engineering News 2003, 23:47-48.
Dowd et al. "Delineating the Specific Influence of Virus Isoelectric Point and Size on Virus Adsorption and Transport through Sandy Soils." Appl. Environ. Microbiol. 1998, 64(2):405-410.
Earnshaw et al. "The Size of the Bacteriophage T4 Head in Solution with Comments about the Dimension of Virus Particles as Visualized by Electron Microscopy." J. Mol. Biol. 1978, 122:247-253.
Endres et al. "Evaluation of an Ion-Exchange Membrane for the Purification of Plasmid DNA." Biotechnol. Appl. Biochem. 2003, 37, 259-266.
Etzel, M.R. "Layered Stacks." Monolithic Materials: Preparation, Properties and Applications, F. Svec, T.B. Tennikova and Z. Deyl (eds.), Ch 10, Elsevier Science, Amsterdam (2003).
Fischer, J. "Separation of Nanometer-Sized Biological Particles Using Membrane Chromatography: An Analysis of Adsorption Kinetics." M.S. Thesis, Univ. Wisconsin (2001).
Fogler, H.S. Elements of Chemical Reaction Engineering. 2d ed. Prentice-Hall, Englewood Cliffs, NJ, 1992.
Gerba, C.P. "Applied and Theoretical Aspects of Virus Adsorption to Surfaces." Adv. Appl. Microbiol. 1984, 30, 133-168.
Ghosh, R. "Protein separation using membrane chromatography: opportunities and challenges." J. Chromat. A 2002, 952:13-27.
Heister et al. "Saturation performance of ion-exchange and adsorption columns." Chem. Eng. Prog. 1952, 48:505-516.
Hermanson et al. Immobilized Affinity Ligand Techniques. Academic Press, San Diego, 1992.
Huyghe et al. "Purification of a Type 5 Recombinant Adenovirus Encoding Human p53 by Column Chromatograhy." Human Gene Therapy 1995, 6:1403-1416.
Johansson et al. "Preparation and Characterization of Prototypes for Multi-Modal Separation Media Aimed for Capture of Negatively Charged Biomolecules at High Salt Conditions." J. Chromat. A 2003, 1016, 21-33.
Kang et al. "High-Performance Chromatofocusing Using Linear and Concave pH Gradients Formed with Simple Buffer Mixtures II. Separation of Proteins." J. Chromatogr. A 2000, 890:37-43.
Kang et al. "Chromatofocusing Using Micropellicular Column Packings with Computer-Aided Design of the Elution Buffer Composition." Anal. Chem. 2002, 74:1038-1045.
Kang et al. "Chromatofocusing of Peptides and Proteins Using Linear pH Gradients Formed on Strong-Ion Exchange Adsorbents." Biotechnol. Bioeng 2004, 87:376-387.
Kang et al. "High-Performance Cation-Exchange Chromatofocusing of Proteins." J. Chromatogr. A 2003, 991:117-128.
Katti et al. "Protein Surface Area and Retention in Hydrophobic Interaction Chromatography." Chromatographia 1987, 24:646-650.
Liu et al. "Development and Qualification of a Novel Virus Removal Filter for Cell Culture Applications." Biotechnol. Prog. 2000, 16:425-434.
Lundstrom, I. "Models of Protein Adsorption on Solid Surfaces." Prog. Colloid Polym. Sci. 1985, 70:76-82.
Lute et al. "Characterization of Coliphage PR772 and Evaluation of Its Use for Virus Filter Performance Testing." Appl. Environ. Microbiol. 2004, 70:4864-4871.
Lyddiatt et al. "Biochemical Recovery and Purification of Gene Therapy Vectors." Curr. Opin. Biotechnol. 1998, 9:177-185.
Morrow, K.J., "Antibody Technology Highlighted in Europe—Updates in Rational Design, Purification, and Manufacturing Presented at Meeting." Genetic Eng. News 2004, 24:52-56.
O'Leary et al. "Determining the Useful Lifetime of Chromatography Resins: Prospective Small-Scale Studies." BioPharm. 2001, 14:10-15.
Oshima et al. "The Use of a Microporous Polyvinylidene Fluoride (PVDF) Membrane Filter to Separate Contaminating Viral Particles from Biologically Important Proteins." Biologicals 1996, 24:137-145.
Penrod et al. "Whole Particle Microelectrophoresis of Small Viruses." J. Colloid Interface Sci. 1995, 173:521-523.
Phillips et al. "Membrane Adsorber Technology for Trace Impurity Removal Applications." Abstr. Papers Am. Chem. Soc., 225: 116-Biot Part I, Mar. 25, 2003.
Phillips et al. "Performance of a membrane adsorber for trace impurity removal in biotechnology manufacturing." J. Chromat. A 2005, 1078:74-82.
Roper et al. "Separation of biomolecules using adsorptive membranes." J. Chromat. A 1995, 702:3-26.
Sarfert et al. "Mass Transfer Limitations in Protein Separations Using Ion-Exchange Membranes." J. Chromat. A 1997, 764:3-20.
Schnabel et al. "Determination of the pI of Human Rhinovirus Serotype 2 by Capillary Isoelectric Focusing." Anal. Chem. 1996, 68:4300-4303.
Shabram et al. "Analytical Anion-Exchange HPLC of Recombinant Type-5 Adenoviral Particles." Human Gene Therapy 1997, 8:453-465.
Sofer, G. "PDA Virus Filter Task Force Update." Developments in Biologicals 2004, 118:129-131.
Soltys et al. "Equilibrium Adsorption of LDL and Gold Immunoconjugates to Affinity Membranes Containing PEG Spacers." Biomaterials 2000, 21:37-48.
Soltys et al. "In Vitro Characterization of a Membrane-Based Low-Density Lipoprotein Affinity Adsorption Device." Blood Purif. 1998, 16:123-134.
Talbot et al. "From Car Parking to Protein Adsorption: An Overview of Sequential Adsorption Processes." Colloids Surfaces A: Physicochem. Eng. Aspects 2000, 165:287-324.
Thommes et al. "Membrane chromatography—an integrative concept in the downstream processing of proteins." Biotechnol. Prog. 1995, 11:357-367.
Van Regenmortel et al. "Virus Taxonomy, Classification and Nomenclature of Viruses." 7th Ed., Academic Press, San Diego, 2000.
Viera et al. "Affinity Membranes: Competitive Binding of the Human IgG Subclasses to Immobilized Protein G." Ind. Eng. Chem. Res. 2000, 39:3356-3363.
Xu et al. "An Overview of Quantitative PCR Assays for Biologicals: Quality and Safety Evaluation." Developments in Biologicals 2003, 113:89-98.
Yamamoto et al. "Retention Behavior of Very Large Biomolecules in Ion-Exchange Chromatography." J. Chromatogr. A 1999, 852:25-30.
Yang et al. "Analysis of Protein Purification Using Ion-Exchange Membranes." Ind. Eng. Chem. Res. 1999, 38:4044-4050.
Yang et al. "Purification of a Large Protein Using Ion-Exchange Membranes." Ind. Eng. Chem. Res. 2002, 41:1597-1602.

(56) References Cited

OTHER PUBLICATIONS

Yang et al. "Evaluation of Three Kinetic Equations in Models of Protein Purification Using Ion-Exchange Membranes." Ind. Eng. Chem. Res. 2003, 42:890-896.
Zeng et al. "Membrane Chromatography: Preparation and Applications to Protein Separation." Biotechnol. Prog. 1999, 15:1003-1019.
Aleksandriiskii, et al. "Preparation of Fibrous Ion-Exchangers Containing Guanidine Groups." *Khimicheskie Volokna*, No. 1, pp. 29-31, (Jan.-Feb. 1991).
Borrego et al. "Development and Application of New Positively Charged Filters for Recovery of Bacteriophages from Water." *Applied and Environmental Microbiology*, (Apr. 1991) p. 1218-1222.
Burton et al. "Hydrophobic charge induction chromatography: salt independent protein adsorption and facile elution with aqueous buffers." *Journal of Chromatography A*, 814 (1998) 71-81.
Dowd et al. "Delineating the Specific Influence of Virus Isoelectric Poiot and Size on Virus Adsorption and Transport through Sandy Soils," *Applied and Environmental Microbiology*, (Feb. 1998) p. 405-410.
Farrah, S. "Chemical Factors Influencing Adsorption of Bacteriophage MS2 to Membrane Filters." *Applied and Environmental Microbiology*, (Mar. 1982) p. 659-663.
Ferruti, et al. "Prevailing Cationic Agmatine-Based Amphoteric Polyamidamine as a Nontoxic, Nonhemolytic, and "Stealthlike" DNA Complexing Agent and Transfection Promoter." *Biomacromolecules* (2007) 8, 1498-1504.
Guerrier, et al. "New method for the selective capture of antibodies under physiological conditions." *Bioseparation* (2000) 9 211-221.
Kolarz, et al. "Acrylic resins with complexes of guanidyl groups and copper (II)." *Reactive Polymers* 23 (1994) 53-61.
Kolarz, et al. "Synthesis and some sorption properties of anion exchanges with guanidyl ligands." *Reactive & Functional Polymers* 61 (2004) 335-346.
Lukasik, et al. "Influence of Salts on Virus Adsorption to Microporous Filters." *Applied and Environmental Microbiology* (Jul. 2000) p. 2914-2920.
Preston, et al. "Novel Approach for Modifying Microporous Filters for Virus Concentration from Water." *Applied and Environmental Microbiology* (Jun. 1988) p. 1325-1329.
Scholz, et al. "Salt-independent binding of antibodies from human serum to thiophilic heterocyclic ligands." *Journal of Chromatography B*, 709 (1998) 189-196.
Shields, et al. "Characterization of Virus Adsorption by Using DEAE-Sepharose and Octyl-Sepharose." *Applied and Environmental Microbiology* (Aug. 2002) p. 3965-3968.
Shields, et al. "Influence of Salts on Electrostatic Interactions Between Poliovirus and Membrane Filters." *Applied and Environmental Microbiology* (Feb. 1983) p. 526-531.
Spivak, et al. "Molecular Imprinting of Carboxylic Acids Employing Novel Functional Macroporous Polymers." *J. Org. Chem.* (1999) 64, 4627-4634.
Tsumoto, et al. "Effects of Salts on Protein—Surface Interactions: Applications for Column Chromatography." *Journal of Pharmaceutical Sciences*, vol. 96, No. 7 (Jul. 2007).
Zhou, et al. "New Q membrane scale-down model for process-scale antibody purification." *Journal of Chromatography A*, 1134 (2006) 66-73.
Barrett, Olivia J., et al., "Chemical Microarrays to Identify Ligands that Bind Pathogenic Cells," ChemBioChem 2006, 7, 1882-1885.
Chatterjee, S., et al., "Influence of the polyethyleneimine grafting on the adsorption capacity of chitosan beads for Reactive Black 5 from aqueous solutions," *Chemical Engineering Journal* 166 (2011) 168-175.
Kimberly, M., et al., "Determination of pKa Values and Total Proton Distribution Pattern of Spermidine by Carbon-13 Nuclear Magnetic Resonance Titrations," *Anal. Chem.* 1981, 53, 789-793.
Satrijo, A., et al., "Anthryl-Doped Conjugated Polyelectrolytes as Aggregation-Based Sensors for Nonquenching Multicationic Analytes," *J. Am. Chem. Soc.* 2007, 129, 16020-16028.

\* cited by examiner

US 9,375,499 B2

ADSORPTIVE MEMBRANES FOR TRAPPING VIRUSES

CROSS-REFERENCE TO RELATED APPLICATIONS

Priority is hereby claimed to provisional application Ser. No. 60/830,917, filed Jul. 14, 2006, which is incorporated herein by reference.

BACKGROUND

Viral clearance is essential for manufacturing safe, biotechnology-derived pharmaceuticals such as monoclonal antibodies (mAbs), recombinant proteins, fusion proteins, sera and media, and the like. Regulatory agencies worldwide mandate removal of viral contaminants from a host of products headed into commercial markets. The nanometer-scale of viruses complicates their separation from biopharmaceutical intermediates because the viral particles (due to their size) bind only to the surface of chromatography beads. Virus particles are too large to enter the pores of conventional chromatographic beads. Thus, the binding capacity of conventional chromatographic beads for viruses is much smaller than it is for impurities that can enter and bind within the pores.

Chromatographic beads themselves are a relatively expensive commercial product. To operate at peak levels, the beads must have a very nearly monodisperse particle size, in combination with a tightly-controlled pore size. As a consequence, chromatographic beads are designed for regeneration so that they can be re-used over many purification cycles (to keep manufacturing costs down). While this approach does, in fact, keep material costs in check, it is not without drawback. Most notably, when the beads are to be recycled, the virus-ligand binding must be reversible. In short, once the beads are loaded to their full capacity of virions, the beads must be cleaned of the virus particles. Resin cleaning and lifetime validation costs (while cheaper than purchasing new chromatographic resin for each separation) are considerable.

There remains a long-felt, and unmet need, for a virus-trapping medium that has both high-efficiency and high-capacity for trapping virus particles, and is also sufficiently low in cost that it can be implemented as a one-time, disposable medium for removing viral contamination from biological products.

SUMMARY OF THE INVENTION

In contrast to beads, the entire surface of an adsorptive membrane is available for virus binding. At the same time, membranes have a low capacity for small impurities. Adsorptive membranes are also cheaper to manufacture than are controlled-porosity, monodisperse beads. Adsorptive membranes for viral clearance are sufficiently cheap to allow the membranes to be disposable. Thus, ligand candidates for chromatographic beads that are rejected due to their irreversible binding characteristics are ideal candidates for viral clearance using adsorptive membranes.

Thus, the present invention includes using ligands that do not bind mAbs, but do bind virus particles under a range of conductivities and pH values.

One distinct advantage of the present invention is that by establishing bracketed generic conditions for viral clearance by disposable membrane adsorbers, developers of new mAbs (and other biologics) will be able to cite project results in lieu of performing costly and time-consuming validation studies, thereby freeing resources and accelerating the availability of therapeutic products to US health-care consumers.

Thus, the present invention is directed to a disposable, virus-trapping membrane comprising a disposable, micro-porous filter membrane and a ligand immobilized on the membrane. The ligand is dimensioned and configured to irreversibly and selectively bind viruses and simultaneously to have a pKa sufficiently high to repel basic proteins (including antibodies in general and monoclonal antibodies in particular) via electrostatic charge repulsion. It is preferred that the ligand is a multi-modal anion-exchange ligand and that the ligand has a positive charge at pH 7. The ligand also preferably has a pKa of at least 10.0.

The filter membrane itself may be fabricated from any suitable, non-reactive material. Preferably, the membrane is fabricated from a polymeric substrate material, for example a polymer substrate selected from the group consisting of polyvinylidene difluoride, polytetrafluorethylene, polyamides, polyamide-imides, polysulfones, polyethersulfones, and polyphenylsulfones.

It is preferred that the ligand is dimensioned and configured to yield a log-reduction value (LRV) of at least 1.0 for neutral viruses disposed in a solution comprising up to 50 mM salt, and more preferably up to 150 mM salt. It is more preferred still that the ligand is dimensioned and configured to yield a log-reduction value (LRV) of at least 5.0 for neutral viruses disposed in a solution comprising up to 50 mM salt and more preferably up to 150 mM salt.

The ligand may be selected from the group consisting of tyrosinol, tryptophanol, octopamine, 2-aminobenzimidazole, 1,3-diamino-2-hydroxypropane, tris(2-aminoethyl)amine, and agmatine. Tris(2-aminoethyl)amine and agmatine are most preferred.

The invention is also directed to a corresponding method of using the membranes described herein to trap viruses, thereby removing them from a solution. Thus, the invention is also directed to a method of removing viruses from a solution suspected of containing viruses, the method comprising contacting a solution suspected of containing viruses with virus-trapping membrane comprising a disposable, micro-porous filter membrane and a ligand immobilized on the membrane, wherein the ligand is dimensioned and configured to irreversibly and selectively bind viruses, and has a pKa sufficiently high to repel basic proteins present in the solution via electrostatic charge repulsion.

As noted earlier with respect to the membrane itself, in the method it is preferred that the solution is contacted with the virus-trapping membrane for a time sufficient to a yield log-reduction value (LRV) of at least 1.0 for neutral viruses disposed in the solution when the solution comprises from 0 to about 50 mM salt, and more preferably still to a yield log-reduction value (LRV) of at least 1.0 for neutral viruses disposed in the solution when the solution comprises from 0 to about 150 mM salt. It is still more preferred that the solution is contacted with the virus-trapping membrane for a time sufficient to a yield log-reduction value (LRV) of at least 5.0 for neutral viruses disposed in the solution when the solution comprises from 0 to about 50 mM salt, and more preferably still to a yield log-reduction value (LRV) of at least 5.0 for neutral viruses disposed in the solution when the solution comprises from 0 to about 150 mM salt.

The filter membrane preferably comprises polyvinylidene difluoride (PVDF), although it may be fabricated from any non-reactive, micro-porous filter membrane material now known or developed in the future. Illustrative filter membrane materials include (without limitation), PVDF (e.g., "KYNAR FLEX"®-brand PVDF, commercially available from Arkema, Inc., King of Prussia, Pa.), polytetrafluorethylene (PTFE), other fluorinated polymers, polyamides (e.g., nylon), polyamide-imides, polysulfones, polyethersulfones, polyphenylsulfones, and the like.

DETAILED DESCRIPTION

Figure 1:
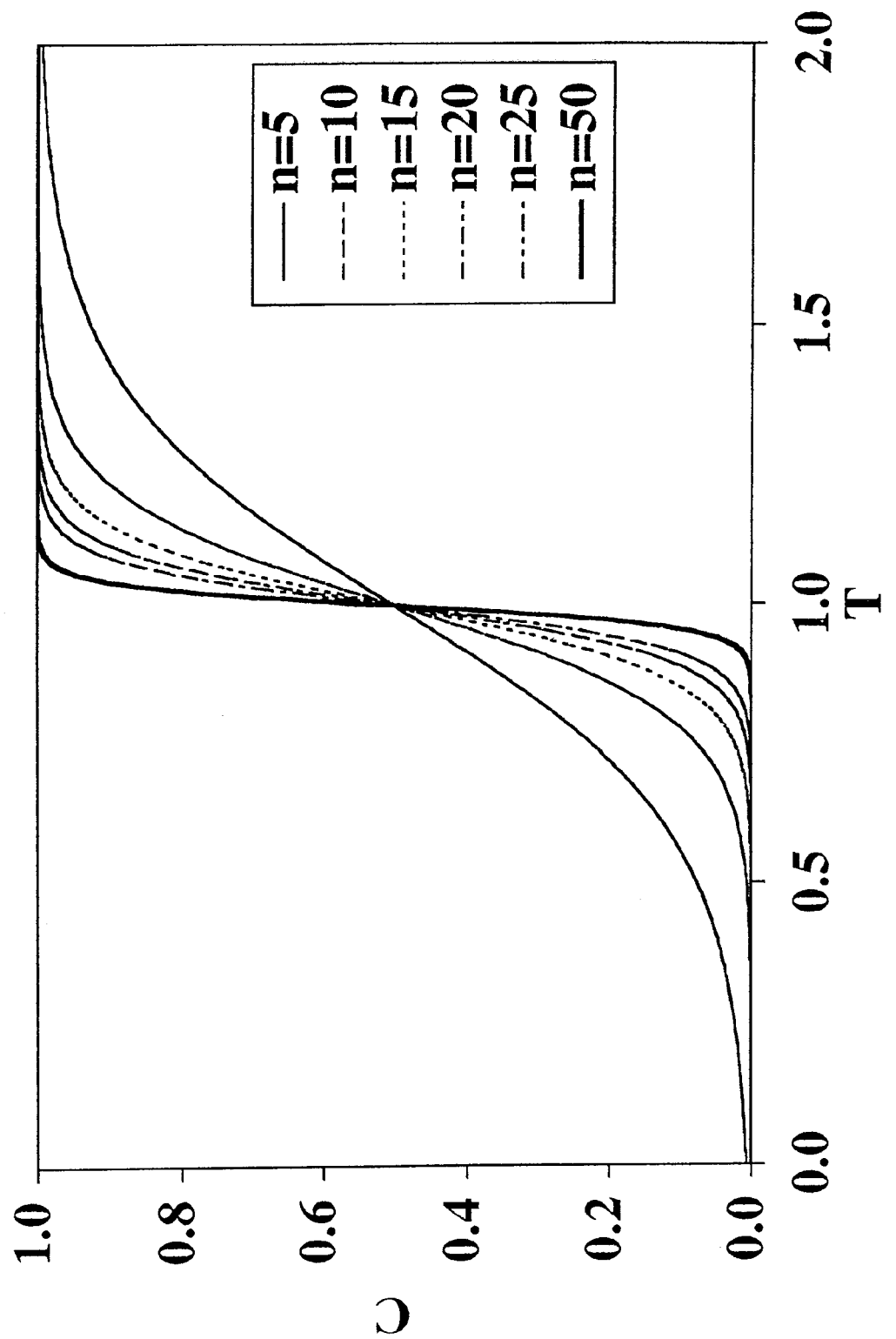
FIG. 1 is a graph depicting breakthrough curves predicted using Eqn. 1 for various values of the dimensionless number of transfer units "n." Larger values for "n" yield sharper breakthrough curves.

Most chromatographic separations utilize columns packed with beads. The bead diameter is an important factor: small beads result in fast diffusion times and large numbers of theoretical plates, but also high pressure drops. Large beads are used in process scale separations to allow for increased flow rates without incurring high pressure drops and the resulting bed compression and eventual plugging. However, large beads have long diffusion times, low plate numbers, and low dynamic capacities. In 1988, membrane chromatography was first introduced as a means to overcome the limitations of column chromatography (Brandt et al., 1988). Microporous membranes containing immobilized ligands were used as the chromatographic media. Because the membranes were thin (~0.1 mm), pressure drop limitations were not significant. Diffusion limitations were eliminated because solute was transported through the pores of the membrane by convection not diffusion. The first devices were hollow fiber membranes where the surface was activated for affinity ligand attachment.

Membrane chromatography has evolved since 1988. Several reviews of membrane chromatography spell out the evolution of the technology over the years. (See, e.g., Etzel 2003, Ghosh 2002, Zeng et al. 1999, Charcosset 1998, Roper 1995, Thommes 1995.). Single-layer and hollow-fiber devices were abandoned because of poor performance. Affinity chromatography gave way to ion exchange chromatography as the primary ligand type. Vendor promotion turned away from protein purification to purification of large biomolecules such as plasmid DNA, viruses, and very large proteins (>250 kDa) where chromatography beads have low capacity. Applications such as viral clearance and purification of gene therapy vectors are examples. Three primary vendors have emerged for membrane chromatography products: Millipore Corporation (Bedford, Mass., USA, "INTERCEPT"®-brand products), Pall Biopharmaceuticals (East Hills, N.Y., USA, "MUSTANG"®-brand products), and Sartorius AG (Goettingen, Germany, "SARTOBIND"®-brand products). The principles and experimental methods applicable to membrane chromatography are presented herein to provide a more complete disclosure of the present invention.

Two key advantages of membrane chromatography over columns packed with beads are: (1) mass transfer limitations are reduced or eliminated leading to fast binding of the solute to the ligand sites on the membrane surface; and (2) low trans-membrane pressure drop. For the target solute to be captured by the binding sites on the membrane surface, the solute must flow into the pore structure, diffuse to the wall of the pore, and bind to the ligand. The result of this process is that the solution passing out of the membrane (the effluent) is less concentrated in the solute than is the feed solution. The breakthrough curve (BTC) is a plot of the solute concentration in the effluent solution versus either time or effluent volume. Ideally the BTC is sharp, meaning no solute comes out in the effluent solution until the membrane reaches saturation, at which point the solute concentration in the effluent solution is the same as in the feed solution. The extent to which this is not the case is a measure of the impact of slow adsorption kinetics, slow mass transfer, and mixing in the flow system. The faster the flow rate, the more likely the BTC will be broad. The following paragraphs present the principles of mass transfer, adsorption kinetics, and mixing in the flow system in the context of describing the sharpness of the BTC.

A simple algebraic model of the BTC can be derived for the case of irreversible adsorption in the absence of axial dispersion in the membrane, mass transfer limitations, and mixing in the flow system (Heister & Vermeulen 1952). This model was derived from the continuity equation using Langmuir adsorption kinetics as the constitutive relation:

$$C = \frac{1}{1 + (1 - e^{-n})e^{n(1-T)}}, \qquad (1)$$

where $C=c/c_0$, c=effluent concentration, $c_0$=feed solution concentration, n=dimensionless number of transfer units, and T=dimensionless throughput. Axial dispersion in the membrane is typically negligible, and irreversible adsorption is often a good approximation for process scale protein purification, because the equilibrium dissociation constant is small for tight binding, and $c_0$ is large. Therefore the ratio $c_0/K_d$ approaches infinity, and adsorption is essentially irreversible. The parameter T for irreversible adsorption ($c_0/K_d \gg 1$) is given by the equation:

$$T = \frac{\varepsilon c_0}{(1-\varepsilon)c_1}(\tau - 1), \quad (2)$$

where $\varepsilon$ is the void fraction of the membrane, and $c_1$ is the total ligand capacity of the membrane based on the solid volume of the membrane. The throughput parameter is a measure of the loading of the membrane. It is the ratio between the amount of solute loaded into the membrane via the feed solution and the maximum amount of solute that can bind to the membrane. The dimensionless time is defined by $\tau = vt/L$, where v is the interstitial liquid velocity, L is the membrane thickness, and t is time.

The parameter n (number of transfer units) is given by the equation:

$$n = \frac{(1-\varepsilon)k_a c_1 L}{\varepsilon v}, \quad (3)$$

where $k_a$ is the association rate constant of the solute with the ligand. The parameter L/n is the height of a transfer unit, comparable to the height equivalent to a theoretical plate (HETP) commonly found in the chromatography literature. When n is large, or HETP is small, breakthrough curves and elution peaks are sharp.

Equation (1) is plotted for various values of n in FIG. 1. The BTC is reasonably sharp when n=20-25. Not much is gained by going to n=50 and beyond. Increasing n requires a high capacity ($c_1$), a fast association rate constant ($k_a$), and a long residence time in the membrane (L/v). If a high flow rate is desired, as is usually the case, then one or more of the other parameter values must have a large value. Thus, most chromatographic membranes use ion exchange binding (high $k_a$), a high ligand density (high $c_1$), and several layers (high L) to achieve sharp BTCs at high flow rates (high v).

The assumption of irreversible adsorption made in the derivation of Eqn (1) is valid for values of $c_0/K_d$ approaching infinity. The practical cut-off for when $c_0/K_d$ is large enough was determined to be $c_0/K_d > 60$, set by the criteria that Eqn (1) fall within 95% of the exact solution at C=0.1 for finite values of $c_0/K_d$. In other words, the exact solution for C=0.1 was used to find T, and then the value of C from Eqn (1) at that T had to be within 95% of the exact solution.

To eliminate mass transfer effects, the residence time in the membrane (L/v) must be much greater than the time scale for diffusion from the center of the membrane pore to the wall:

$$L/v \gg d_p^2/4D \quad (4)$$

where $d_p$ is the diameter of the pore and D is the diffusion coefficient of the solute. This situation is frequently not the case when the membrane is thin (small L), the pores are large (large $d_p$), and operation is at high flow rate (large v). Most membrane chromatography systems are operated at residence times of 1 to 10 seconds. Membrane pore sizes of less than 1 µm eliminate mass transfer limitations for large proteins when residence times are about 1 second or longer. However, some membranes have a pore size of about 5 µm, in which case residence times of about 100 seconds or longer are required to obtain sharp BTCs for large proteins. For very large biomolecules such as plasmid DNA and viruses, even longer residence times are needed because D is smaller. As a rule of thumb, D is approximately proportional to the inverse of the molecular mass raised to the ⅓ power. Therefore, systems separating small proteins such as alpha-lactalbumin (14.4 kDa, D=1.1×10⁻⁶ cm²/s) can be operated at higher flow rates than systems separating large proteins such as thyroglobulin (660 kDa, D=2.5×10⁻⁷ cm²/s).

A few examples illustrate the use of Eqn (4). BTCs were sharp when alpha-lactalbumin and thyroglobulin were captured onto a chromatographic membrane having a pore size $d_p$=0.65 µm, a stack thickness L=0.098 cm, and operated at velocity v=4.9×10⁻³ cm/s (Yang et al. 2002).

On one hand, the time scales for diffusion (4 ms for thyroglobulin and 1 ms for alpha-lactalbumin) were much smaller than the residence time in the membrane (L/v=20 s). On the other hand, BTCs were broad when thyroglobulin was captured onto a chromatographic membrane having a pore size of 5 µm, a stack thickness of 0.06 cm, and operated at a velocity of 4.2×10⁻² cm/s. In this case, the time scale for diffusion (0.25 s) was too close to the residence time in the membrane (L/v=1.4 s). Even at a residence time of 14 seconds the BTC was not sharp for this system, which indicates that the residence time in the membrane needs to be much greater than the time scale for diffusion to obtain a sharp BTC.

Figure 2:
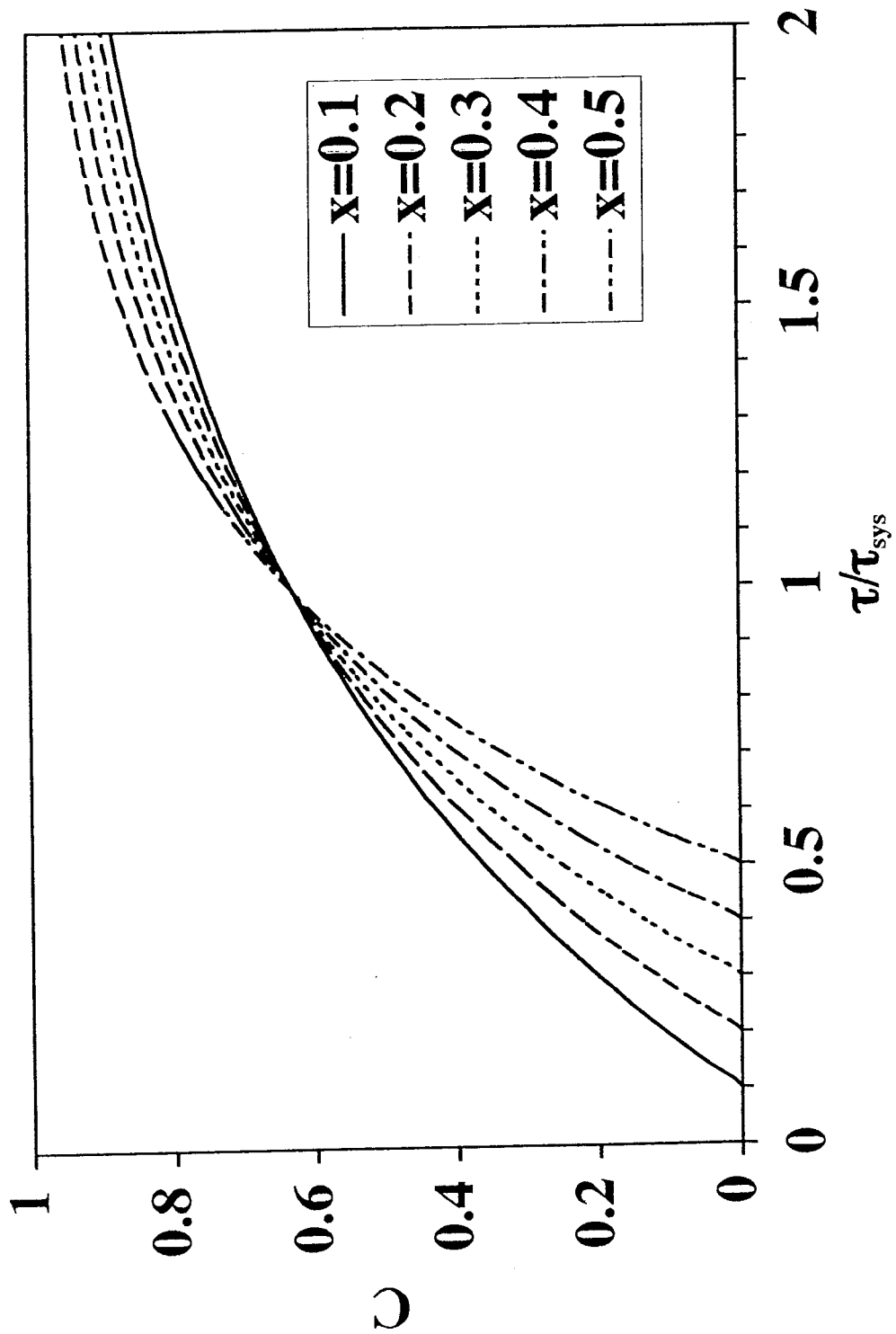
FIG. 2 is a graph depicting breakthrough curves predicted using Eqn. 5 as a function of the fraction unmixed volume ("x"), where $\tau_{sys}$ is the system mean residence time.

Broad BTCs can result solely from liquid mixing in the pump, tubing, fittings, membrane holder, stack of membranes, and detector system. For example, if the liquid flowing through the membranes has different residence times, e.g. shorter times through the center and longer times through the edges, then it will broaden the BTC. The simplest model found to describe mixing in the flow system in membrane chromatography is the serial combination of a continuously stirred tank reactor (CSTR) and an ideal plug flow reactor (PFR) (10):

$$C = 1 - \exp\left(\frac{x - (\tau/\tau_{sys})}{1-x}\right), \quad (5)$$

where $\tau_{sys}$ is the dimensionless mean residence time in the system, and x is the fraction PFR volume ($x = \tau_{PFR}/\tau_{sys}$). After the delay time=$x\tau_{sys}$, from the dead volume, Eqn (5) can be used to predict the BTC for a non-binding tracer. Prior to that time ($\tau \le x\tau_{sys}$) C=0 (FIG. 2). Typically, mixing in the flow system is not a significant factor in determining the shape of the BTC because $x\tau_{sys}$ is small compared to the values of $\tau$ at the point of breakthrough, defined as when C=0.1.

The following example illustrates how to conduct an experiment and analyze the results. Data were taken from the literature for capture of a small protein (alpha-lactalbumin) by an anion exchange membrane (Yang et al. 2002).

Flat-sheet polyvinylidene difluoride membranes (acylimidazole activated "DURAPORE"®-brand membranes, Millipore, Bedford, Mass.) were reacted with 2-amino-ethyltrimethylammonium chloride to make the anion exchange membranes. These membranes were 140 µm thick and had a pore size of 0.65 µm, an internal surface area of 155 cm² per cm² of frontal area, and a void fraction of $\varepsilon$=0.7. A 7-layer stack of these 25 mm diameter membranes sandwiched between 2 blank membranes upstream and downstream (11 membrane discs total) was placed into a membrane holder. The blank membranes aided in flow distribution. Protein solution (0.05 g/L alpha-lactalbumin in 50 mM Tris, pH 8.3) was loaded into the membrane stack at a flow rate of 1 mL/min, and the absorbance at 280 nm of the effluent solution measured versus time. Mixing in the flow system was measured by loading a non-binding tracer (0.05 g/L alpha-lactalbumin in 50 mM Tris, 2 M NaCl, pH 8.3).

Figure 3:
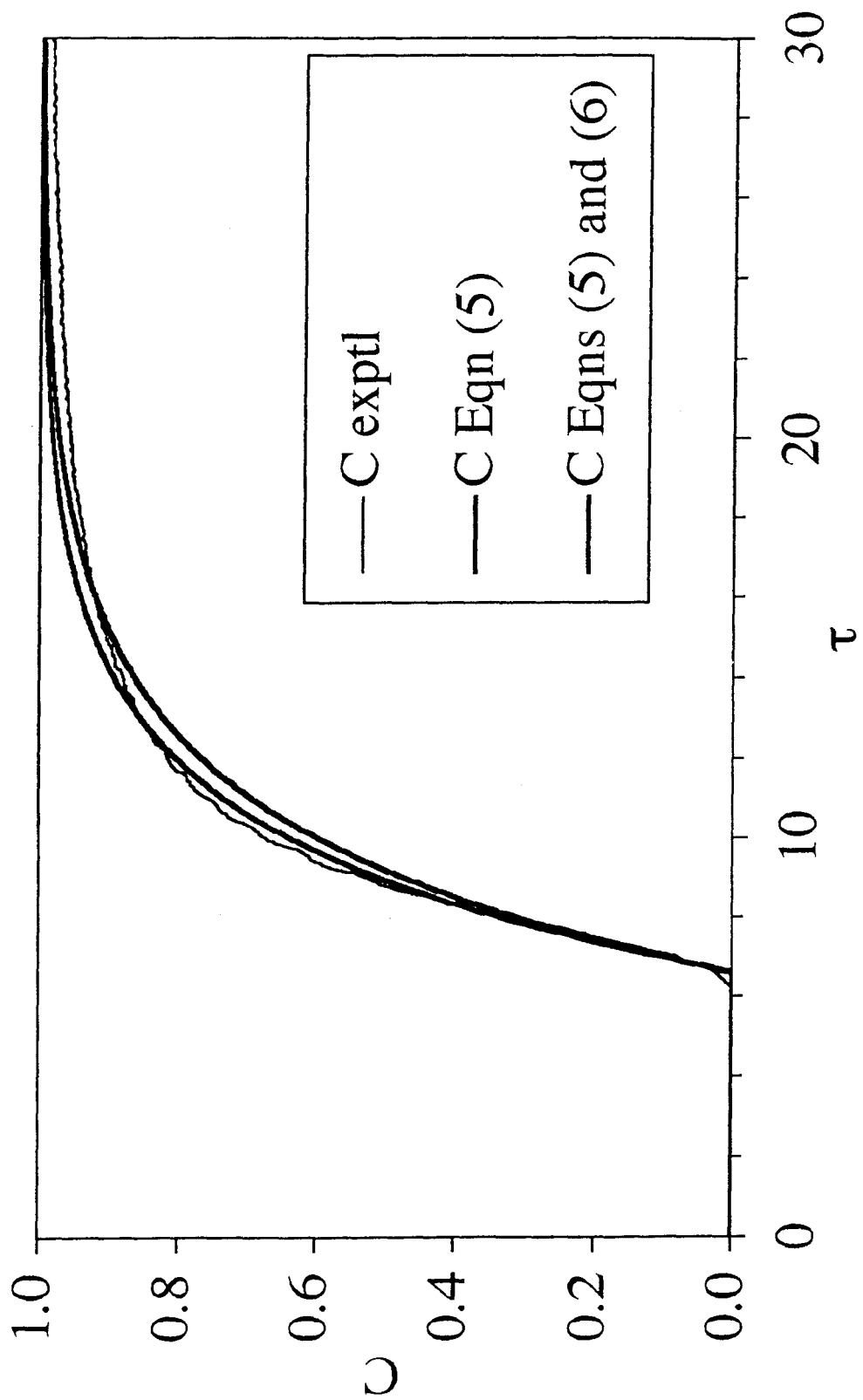
FIG. 3 is a graph depicting experimental breakthrough curves for a non-binding tracer superimposed upon fitted curves using Eqn. 5 alone and Eqns. 5 and 6 combined.

The response to loading a non-binding tracer was fit using Eqn (5) resulting in a fraction PFR volume of x=0.67 and a dimensionless residence time for the system of $\tau_{sys}$=9.4 (see FIG. 3). To generate this plot from the raw data, the voltage signal from the detector was determined for the baseline ($V_{BL}$) using only buffer without protein, and the feed solution ($V_{FS}$) while bypassing the membrane holder. Then the voltage signal from the BTC was converted to C using the equation $C=(V-V_O)/(V_{FS}-V_O)$. This conversion assumes that absorbance is linearly related to protein concentration, which is a valid assumption for dilute protein solutions (c<2 g/L) as was the case in this example ($c_0$=0.05 g/L). The x-axis was obtained by converting time to dimensionless time $\tau$(=vt/L) using the values of v=4.85×10³ cm/s (v=Q/εA where Q=1 mL/min, ε=0.7, and A=4.91 cm²) and L=0.098 cm (=7×140 μm).

The values of x and $\tau_{sys}$ mentioned above were obtained using the SOLVER function in Microsoft Excel software to minimize the sum of the square of the difference between the model and the data (least squares method). Another perhaps more accurate method is to obtain $\tau_{sys}$, from the first moment of the data using the equation:

$$\tau_{sys} = \int_0^\infty (1-C)d\tau = \int_0^1 \tau dC. \qquad (6)$$

Then this calculated value of $\tau_{sys}$, is used along with Eqn (5) to fit the data by using x as the only fitted parameter value in Excel. Using this method, $\tau_{sys}$, =10.3 and x=0.638. This result is also plotted in FIG. 3 and is nearly identical to the first method.

Frequently, rather than reporting liquid volumes directly, the volumes are normalized by dividing by the membrane volume. This makes the results dimensionless and independent of scale. The volumes are then referred to in terms of "membrane volumes." For example, to normalize the effluent liquid volume and express it in terms of membrane volumes, divide it by the membrane volume: (effluent volume)÷(membrane volume)=ετ. When the system volume is normalized and expressed in terms of membrane volumes, it is equal to: $\epsilon\tau_{sys}$=7.2 membrane volumes for these data (Yang et al. 2002). Of this, $x\epsilon\tau_{sys}$; =4.6 membrane volumes is the PFR portion, which includes 1 membrane volume for the stack of 7 membranes, and (1−x) $\epsilon\tau_{sys}$, =2.6 membrane volumes is the CSTR portion. One membrane volume equals 0.481 mL in this experiment. In conclusion, if the value of τ at the point of breakthrough (C=0.1) is much greater than $x\tau_{sys}$, =6.3 to 6.6, then mixing in the flow system can be neglected.

To ignore mass transfer effects, Eqn (4) must be satisfied. For the experimental system described herein, L/v=20 s, and the RHS of Eqn (4) is 1 ms=[0.65×10⁻⁴ cm)²/4(1.1×10⁶ cm²)]. Therefore, the time scale for convection in the membrane is 20,000 times greater than the time scale for boundary layer mass transfer to the wall of the pores, and mass transfer can be safely neglected. Based on this calculation, a greater flow rate than 1 mL/min, perhaps even 200 mL/min, could have been used and still not have a mass transfer limitation. Thus, although the flow rate used was 125 membrane volumes per hour, it might have been possible to use 25,000 membrane volumes per hour without encountering a mass transfer limitation. Column chromatography using beds of packed beads typically operates at flow rates of 30 column volumes per hour, much lower than the flow rates possible using membrane chromatography.

The experimental BTC for alpha-lactalbumin is shown in FIG. 3. The point of breakthrough (C=0.1) occurred at τ=93.6. This value is 14 to 15 times greater than $x\tau_{sys}$ which means that mixing in the flow system can be neglected as a factor in determining the shape of the BTC. The point of breakthrough occurred at 66 membrane volumes (=ετ). The dynamic binding capacity of the membrane is then $\epsilon\tau c_0$ or 3.3 mg/mL expressed as mg bound per mL of membrane.

To fit Eqn (1) to the BTC, values of the two unknowns ($k_2$ and $c_1$) were assumed temporarily, allowing calculation of T using Eqn (2) and n using Eqn (3). The other parameter values (ε, $c_0$, v, L, and τ) are already known. Using the temporary values of T and N, Eqn (1) was used to calculate C. Then SOLVER in Excel was used to minimize the square of the differences between the calculated and observed values of C using $K_a$ and $c_1$ as fitted parameters. The solution found was $k_a$=1900 M⁻¹s⁻¹ and $c_1$=0.00085 M. The value of n was 14.

Figure 4:
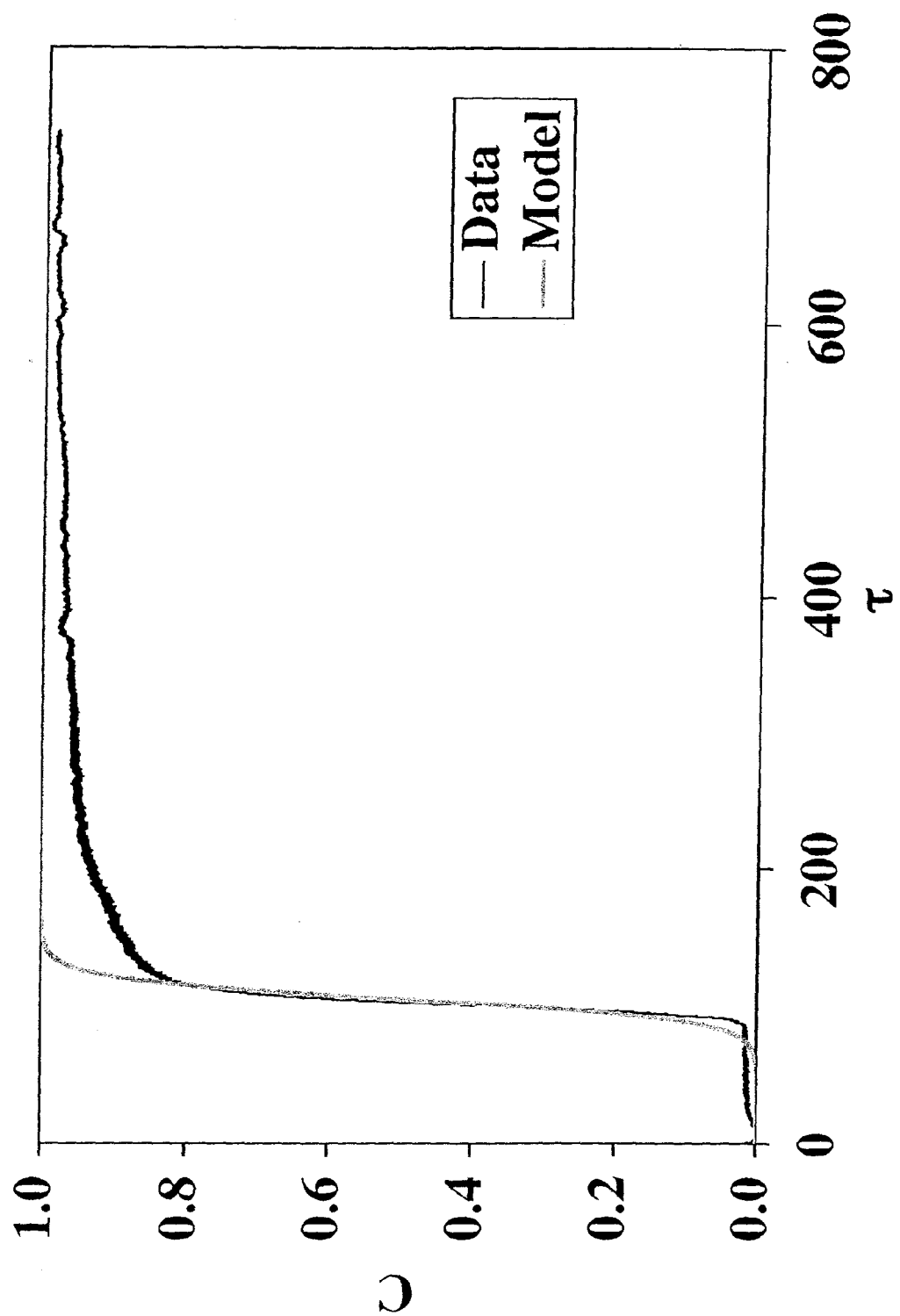
FIG. 4 is a graph depicting an experimental breakthrough curve for alpha-lactalbumin superimposed upon a fitted curve using Eqn. 1.

The fitted value for $c_1$=0.00085 M is expressed as moles of alpha-lactalbumin bound per L of membrane solid volume. The solid volume of the membrane divided by the total volume of the membrane equals (1−ε). Therefore, the fitted value of the membrane capacity is 3.7 mg/mL when expressed on a mass and total-membrane-volume basis (=(1−ε)$c_1$). This value corresponds closely to the value of 3.3 mg/mL determined from the point of breakthrough as mentioned above. In conclusion, the fitted and observed binding capacities match, which provides validation of the model and the fitted parameter values. The BTC was not symmetric. Instead, the BTC first rose sharply toward C=0.6-0.8, and then rose slowly toward, but never reached C=1.0 (see FIG. 4).

Successful scale-down and scale-up of membrane chromatography systems requires an accurate, scientifically based model. Eqns (1)-(6) can be used for this purpose. To obtain equal BTC performance (C vs. time is the same), the values of n and T must match at each time point for the small- and large-scale, and mixing in the flow system (x and $\tau_{sys}$) must be either the same or small enough to be negligible. When the same membrane material and feed stream are used at large- and small-scale, parameters such as $c_0$, ε, $c_1$, $k_a$, $d_p$, and D will most likely be constant. However, v, L, x, and $\tau_{sys}$, may not be constant, because the flow rate, number of layers in the membrane stack, and extent of mixing in the flow system may increase with increasing scale. However, if L/v is kept constant, and mixing in the flow system is verified to be negligible, then equal performance at different scales is expected. The impact of potential deviations in operating parameters ($c_0$ and v), and membrane chromatography device parameters (ε, $c_1$, $k_a$, $d_p$, and L) can then be evaluated using the model, and used to steer clear of regions where performance is too sensitive to normal variation.

As noted earlier, the potential for contamination of therapeutic proteins produced in cell culture by viruses is a regulatory concern. Steps are included in downstream processing specifically to meet regulatory requirements; redundant and complementary unit operations are included that clear any potential viral contaminant from the protein product. For viral clearance applications, performance is measured by the log reduction value (LRV), which is simply LRV=−Log₁₀(C). Typical LRV values for anion exchange column chromatography are LRV=4 to 6 (Curtis et al. 2003).

The assumption of irreversible adsorption made in the derivation of Eqn (1) is valid for values of $c_0/K_d$ approaching infinity, as mentioned above. This is a good assumption for the BTC in process-scale protein separations where the feed solution is concentrated. In contrast, in viral clearance operations, the feed solution typically contains very small concentrations of virus (pM to nM). Therefore, depending on the value of $K_d$, two limiting cases are possible: (1) $C_0/K_d \gg 1$ and irreversible adsorption; and (2) $c_0/K_d \ll 1$ and linear adsorption.

For irreversible adsorption, where $c_0/K_d$ approaches infinity, the practical cut-off for when $c_0/K_d$ is large enough was found to be $c_0/K_d > 30$, determined by setting the criteria that Eqn (1) fall within 95% of the exact solution at LRV=4. The mathematical relationship between LRV, T, and n for irreversible adsorption can be derived from Eqn (1):

$$LRV \approx \frac{n(1-T)}{\ln(10)} \quad (7)$$

Figure 6:
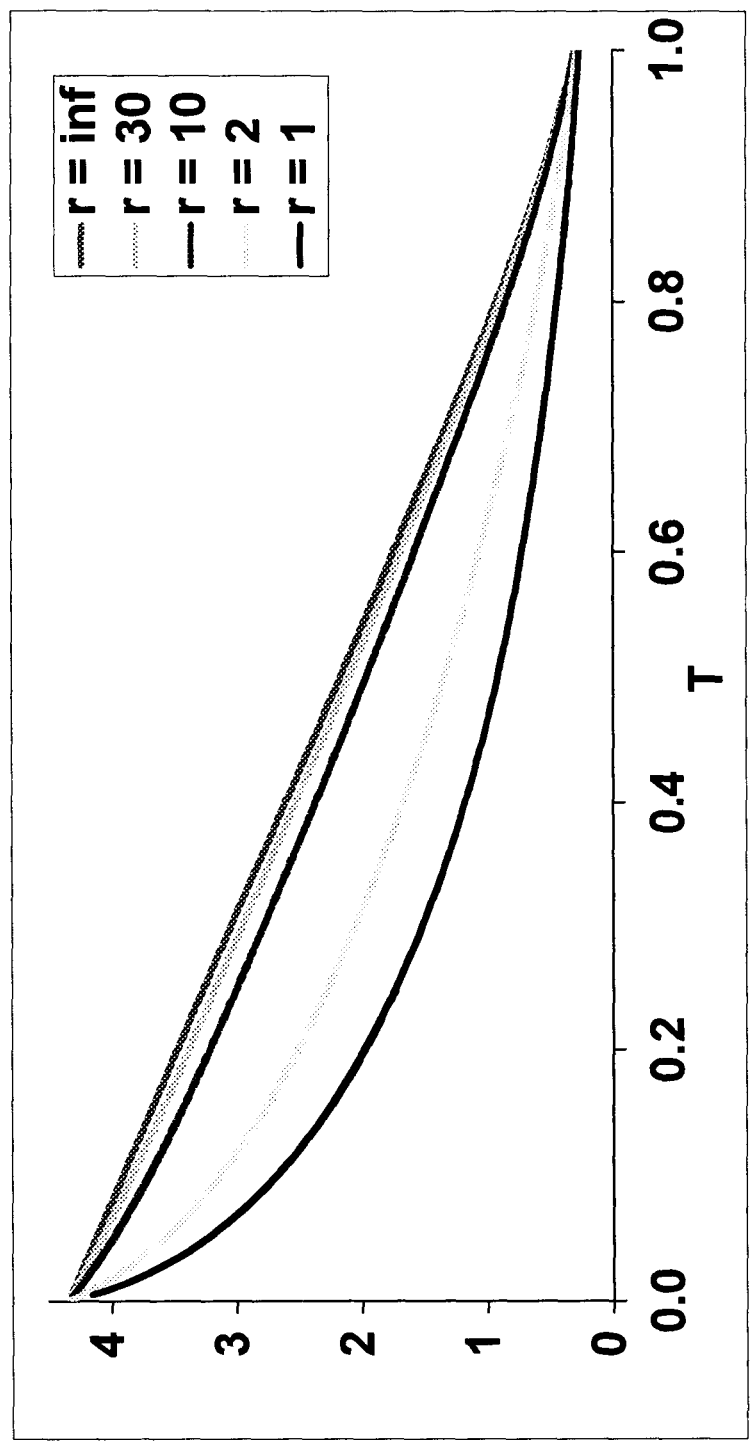
FIG. 6 is a graph depicting the calculated decline in LRV versus the throughput parameter (T) for an adsorptive membrane for trapping viruses when adsorption is reversible (r=1) and irreversible (r=infinity). Irreversible adsorption is desired for virus removal because the LRV is greater at any given throughput, and the throughput is greater at a given LRV when adsorption is irreversible rather than reversible.

Eqn (7) reveals that there is a linear decline in LRV with increasing T. The slope of this plot is approximately $-n/\ln(10)$, and the y-intercept is approximately $n/\ln(10)$. See FIG. 6.

For irreversible adsorption, Eqn (2) can be rearranged to find the number of membrane volumes processed (ET) at any value of the parameter T when $\tau \gg 1$:

$$\varepsilon\tau\bigg|_{irreversible} \approx \frac{T(1-\varepsilon)c_1}{c_0} \quad (8)$$

The parameter T in Eqn (8) is a dimensionless measure of the relative amount of material loaded into the membrane. T=0.0 corresponds to the point where the feed solution has just started to emerge at the exit of the membrane. T=1.0 corresponds to the point where the total mass loaded into the membrane equals the total membrane capacity. For an infinitely sharp BTC ($n \to \infty$), T=1.0 also corresponds to 100% saturation of the membrane. However, this is impractical. A practical target for operation can be found by examination of Eqn (7). Practically speaking, a LRV=4, in combination with a large loading capacity is suitable for most applications. For example, the experiment described herein attained LRV=4 at T=0.08 and n=10, or at T=0.90 and n=90. Therefore, it is desirable to have a large value of n because a much larger throughput (greater T) can be achieved, while still attaining LRV=4. To attain 90% of the saturation capacity (T=0.9) at LRV=4.0, Eqn (7) reveals that the 90% saturation capacity requires attaining a value of n=92.

From Eqn (3), attaining n=92 requires a high capacity ($c_1$), thick membrane stack (L), low flow rate (v), and fast adsorption rate constant ($k_a$). For example, for the membrane system analyzed in section 3, the invariant membrane parameters are: $k_a=1900$ M$^{-1}$s$^{-1}$, $c_1=0.00085$ M, and $\varepsilon=07$. Therefore, to attain the above target (LRV=4 at T=0.9) requires L/v=133 s. This residence time is much longer than the time used in the experiment (L/v=20 s). This example illustrates a general rule of thumb: it is easier to obtain a sharp BTC for protein purification than it is to achieve a target LRV for viral clearance.

For the linear adsorption case where $C_0/K_d \ll 1$, Eqn (1) is not valid. In this case, the BTC is given by:

$$C = 1 - \exp(-nT)\int_0^n \exp(-\eta)I_0(2\sqrt{\eta nT})d\eta, \quad (9)$$

where $I_0$ is the modified Bessel function of zero order. Values of n and T that result in LRV=4 were calculated from Eqn (9).

In general, when LRV=4 for any given value of n, the corresponding value of T is smaller in the linear adsorption case than the irreversible adsorption case. In other words, as in the irreversible adsorption case of Eqn (7), LRV for the linear adsorption case is a function of only n and T, but the values of LRV for the linear adsorption case are generally smaller at a given value of n and T. Only when T=0 is the LRV for the linear adsorption case equal to the LRV for the irreversible adsorption case. This is because when T=0, Eqn (9) reduces to $C=\exp(-n)$, because $I_0(0)=1$, and LRV=$n/\ln(10)$, which is the same result as Eqn (7) when T=0.

The definition of T is different for the linear adsorption case:

$$T = \frac{\varepsilon K_d}{(1-\varepsilon)c_1}(\tau - 1), \quad (10)$$

where $K_d$ is the dissociation equilibrium constant Eqn (10) can be rearranged to calculate the membrane volumes of feed solution processed at any value of T when $\tau \gg 1$:

$$\varepsilon\tau\bigg|_{linear} \approx \frac{T(1-\varepsilon)c_1}{K_d} \quad (11)$$

We can see from Eqn (11) that the volume of feed solution processed at a given value of T is not related at all to the feed solution concentration for the linear case, whereas for the case of irreversible adsorption it was inversely related to the feed solution concentration as in Eqn (8). Also, because $K_d \gg c_0$ for the linear adsorption case, throughput expressed as $\varepsilon\tau$ or T is going to be lower than for the irreversible adsorption case.

From a regulatory perspective, if a membrane chromatography product was shown to attain LRV=4 for a particular feed solution at a fixed concentration ($c_0$), loading volume ($\varepsilon\tau$), and residence time (L/v), then the LRV should exceed 4 for a smaller loading volume, longer residence time, or more dilute feed solution. Validation of a membrane chromatography system for viral clearance should utilize measuring the LRV of effluent fractions over time rather than the entire effluent pool, and the trend of LRV vs. T can be determined to aid in setting allowable operating limits.

From a membrane design point of view, we have set the above target (LRV=4.0 and T=0.9), but need to set some additional constraints to fully define the problem. For example, what flow rate and volumetric throughput will be attractive compared to competing technologies? One approach to answering this question is to take values for the flow rate and volumetric throughput from the commercially successful viral filtration systems. It should be noted that viral filtration removes viruses by a sieving mechanism, which is totally different than the adsorption mechanism used in membrane chromatography. Nevertheless, the performance capabilities of viral filtration membranes can be used as a target for membrane chromatography systems too. A commercially successful viral filtration system is the "VIRESOLVE"®-brand filters from Millipore (Bedford, Mass.). These filters can achieve LRV=4.0 for the bacteriophage $\phi$X174 when operated at a flow rate of 150 L/m$^2$-h, a throughput of 300 L/m$^2$, and a pressure drop of 2.0 bar (Millipore Technical Brief 2002). This flow rate and throughput target corresponds to $\varepsilon v_{min}=4.2 \times 10^{-3}$ cm/s and $\varepsilon\tau_{min}/L_{min}=30$ cm, respectively, for a membrane chromatography system. One advantage of membrane chromatography is a lower pressure drop. At 2.0 bar, the membrane system analyzed earlier would attain the target flow rate when L=6.2 cm based on the reported hydraulic permeability (Phillips et al. 2005). Therefore, pressure drop is not a limitation.

Eqns (7) and (8) can be used for the irreversible adsorption case, and Eqn (3) to calculate the minimum L under conditions constrained by meeting the targets for flow rate $\epsilon v_{min}$=4.2×10$^{-3}$ cm/s) throughput ($\epsilon \tau_{min} L_{min}$=30 cm), and viral clearance (LRV 4.0) as set above. The data from above is used to illustrate these calculations. The value of $L_{min}$ needed to meet the flow rate and viral clearance targets is found from substitution of LRV=4.0 and T=0.9 into Eqn (7) to obtain n=92, which is then substituted into Eqn (3) along with $\epsilon v_{min}$=4.2×10$^{-3}$ cm/s to solve for $L_{min}$. The value of $L_{min}$ needed to meet the throughput target is found from substitution of $\epsilon \tau_{min} L_{min}$=30 cm into the LHS of Eqn (8). To meet the throughput requirement, the membrane must have an $L_{min}$=0.46 cm. However, this value is too thin to meet the viral clearance target of LRV 4.0, which requires $L_{min}$=0.8 cm. Thus, a membrane stack thicker than $L_{min}$=0.8 cm would exceed the targets set above. The principles outlined herein can be used to guide the design of membrane chromatography systems for viral clearance. Desirable system parameters include: (1) high membrane capacity $c_1$, (2) thick membrane stack L, (3) dilute feed solution $c_0$, and (4) fast association rate constant $k_a$. This is in the case of irreversible adsorption.

The solution is slightly different for the case of linear adsorption. In that case, $K_d$ must be known, Eqn (11) comes into play, and the feed solution concentration does not affect performance. Realistically, the above target (LRV=4 at T=0.9) cannot be obtained in the case of linear adsorption because T<0.9 when LRV=4 for all reasonable values of n. Thus, the throughput T is less at a given value of n and LRV, and the LRV is less at a given value of n and T for the linear adsorption case compared to the irreversible adsorption case. In the linear adsorption case, a value of n may be chosen and the value of T determined when LRV=4. The value of L to meet the viral clearance target is calculated from Eqn (3), and the value of $L_{min}$ to meet the flow rate target is calculated from Eqn (11).

Figure 5:
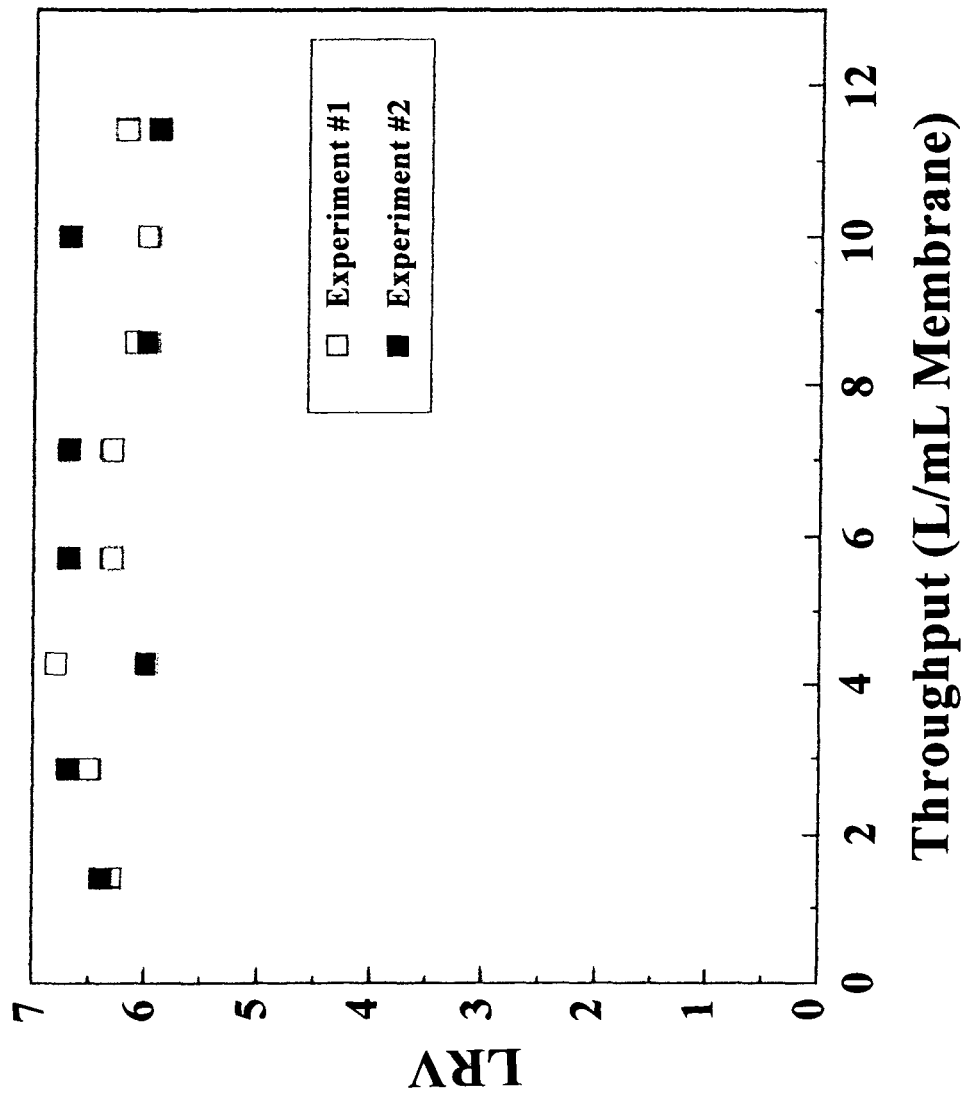
FIG. 5 is a graph depicting log reduction value (LRV) as a function of throughput for the bacteriophage φ174 in 25 mM Tris, pH 8.1, at a flow rate of 3,400 membrane volumes per hour.

The model can be used to analyze data taken from the literature (13), where the LRV was measured for a membrane chromatography system similar to the one described hereinabove. The effect of throughput (=$\epsilon \tau$) on LRV for $\phi$X174 is shown in FIG. 5. The feed solution in this experiment was very dilute: 1.5×10$^7$ pfu/mL ($c_0 \approx 10^{-13}$ M). The membrane capacity was reportedly $c_1$=0.0058 M, measured using tosyl glutamic acid, and L=0.1 cm, and $\epsilon$=0.7. From these values, the parameter T in Eqn (2) can be calculated: T$\approx$4×10$^{-11}$. In essence, T$\approx$0, and LRV=n/ln(10) from Eqn (7). Therefore, the LRV is not a function of throughput T, and this may be why no dependency on T is observed in FIG. 5.

As noted earlier, viral clearance is essential in the manufacture of biotechnology-derived products such as monoclonal antibodies (mAbs). Monoclonal antibody production is currently the fastest growing segment of the U.S. biotechnology industry, with 30% annual growth and over $7 billion in annual sales in 2004 (Das 2003). Regulatory agencies worldwide, including the United States Food & Drug Administration (FDA), mandate a demonstration of freedom from viral contaminants before a new biopharmaceutical product is approved for human use. See Fed. Reg. 63, 51074-51084 (1998). Key components of the assurance of virus safety include specific virus removal steps such as filtration, as well as small-scale studies that measure the clearance capacity and robustness of the virus-removal protocol. In response to the recent plateau of new drug approvals, the FDA has identified a list of important research goals that can accelerate the critical path of pharmaceutical development. The modernization of manufacturing science, including developing improved viral safety strategies, is high on this list of goals.

The nanometer-scale size of virus particles makes separation from biopharmaceutical process intermediates a challenging manufacturing issue. Virus particles bind only to the surface of traditional chromatography beads because they are too large to enter the fine network of pores (Endres et al. 2003; Yamamoto et al. 1999; Lyddiatt and O'Sullivan 1998). Therefore, the binding capacity of porous beads for virus particles is much lower than it is for smaller molecules that can access the full volume of the beads. This phenomenon causes an odd problem: the binding capacity of chromatographic beads is much greater for small impurities, host-cell proteins, and endotoxins, than it is for the far larger target, virus particles (Yang et al. 2003).

Virus particles bind only to the surface of a membrane too, in the same fashion as for beads. However, membranes have a much larger available surface area than do beads. For example, micro-porous membranes have an internal surface area of about 1.1 m$^2$/mL (Soltys and Etzel 2000), compared to about 0.11 m$^2$/mL for a column packed with 90 μm diameter beads. In short, the surface area of the membrane is a full order of magnitude great than the beads. Furthermore, the adsorptive capacity of membranes increases with increasing size of the adsorbed particle because the larger particles form a thicker layer on the membrane surface (Endres et al. 2003). The net effect is that adsorptive membranes have a relatively high capacity for large nanometer-sized particles and a relatively low capacity for small molecules (DePalma 2003). This is the exact opposite of the situation for beads. Thus, the relative advantage of using membranes versus beads increases dramatically as the particle size to be trapped increases. This makes adsorptive membranes well-suited for viral clearance.

Traditional chromatography beads were designed for protein separations, not virus separations (Lyddiatt & O'Sullivan 1998). Adsorptive membranes have the advantage of low cost, small volume, and disposability. Beads, in contrast, were designed for multiple uses. Process economics thus encourages the recycling of beads, often for hundreds (and sometimes for thousands) of cycles (O'Leary et al. 2001). For bead recycling, regeneration is essential. Therefore the ligands immobilized on the beads must bind their target reversibly. Resin cleaning and lifetime validation costs are considerable for beads. These restrictions are absent for adsorptive membranes because they are disposable and do not need to bind the virus reversibly for viral clearance applications. Because reversible binding is not required, irreversible, tighter-binding ligands are practical. The higher dynamic capacity of adsorptive membranes reduces the adsorbent volume, requiring smaller buffer volumes, lower consumption of pharmaceutical-grade water, and less floor space for buffer tanks and pumps. These advantages lead to reduced facility costs, a major expense for bioprocessing. The "pass-through-and-dispose" operational mode also reduces the required equipment space as compared to chromatography columns, which eliminates the need for a dedicated room for this unit operation.

Robust, uniform and predictable viral clearance by membrane adsorbers enables generic and bracketed validation strategies (Anon. 1997). The FDA defines a generic clearance study as a situation wherein virus removal and inactivation is demonstrated for several steps in the purification process of a model antibody. These data may then be extrapolated to other antibodies following the same procedure. A bracketed validation approach is where virus removal/inactivation is demonstrated for a particular module at two different values of a given parameter (e.g. ionic strength, dwell time, temperature, etc.) and may use any values of that parameter falling within that range. Examples of two matrix/bracket studies of robust viral clearance steps (e.g., low pH inactivation and anion exchange chromatography) have been described in the literature (Brorson et al. 2003; Curtis et al. 2003). Bracketing and generic validation of robust virus removal unit operations were proposed by the FDA to streamline and update the overall viral safety assurance strategy for clinical trial-stage mAbs. These approaches can eliminate redundant testing, impart flexibility during product development, and spur product development.

The invention thus has many advantages. For example, using membranes eliminates labor-intensive column packing and validation, reduces floor space and equipment requirements, and lowers overall costs due to streamlined regulatory compliance. Because of their expense, virus removal validation studies are often a stumbling block for smaller firms and independent academic investigators performing early phase studies with novel antibodies. Large biotechnology companies making large quantities of a single or multiple products also benefit greatly from the reduction in cleaning and media lifetime validation costs and decreased use of floor space, buffer components, equipment, tanks and pharmaceutical-grade water.

TABLE 1

Ligand Panel

| Ligand | Aromatic | pKa | Charge at pH 7 |
|---|---|---|---|
| AETMA | No | >12 | + |
| TAEA | No | 7.7, 10.5 | + |
| Tyrosinol | Yes | 10.8 | + |

One strong anion-exchange moiety (2-aminoethyltrimethylammonium chloride, AETMA) and two multi-modal moieties (tris(2-aminoethyl)amine, TAEA; and tyrosinol) serve as examples of ligands (see Table 1). One advantage of the present invention is that the membranes exhibit robust viral clearance, even in the presence of relatively large concentrations of salt (e.g., 150 mM salt). This is important for achieving robust viral clearance because many process solutions used in biopharmaceutical manufacture have conductivities in the range of 15-30 mS/cm. Multi-modal ligands are anion exchangers with secondary interactions such as hydrogen bonding and hydrophobic interactions that make them more salt tolerant (Johansson et al. 2003). Salt tolerance is measured in comparison to the conventional Q ligand (AETMA), which rapidly loses capacity for some viruses (e.g., φX174) at conductivities three- to six-fold less than the target range, e.g. dropping viral clearance from a six log-reduction value (LRV) to a one (1) LRV in going from 0 to 50 mM NaCl (Phillips & Lutz 2003). The Q ligand is a frequent choice for anion exchange chromatography for viral clearance operations (Xu and Brorson 2003; Curtis et al. 2003). The second ligand, TAEA, is a non-aromatic anion-exchange ligand that is positively-charged at pH 7, causing electrostatic repulsion of mAb. TAEA is 25-times more salt tolerant than the Q ligand (Johansson et al. 2003).

The third ligand, tyrosinol, is a good example of a ligand rejected for use in protein purification, but which is highly suitable as a ligand for a disposable, virus-trapping membrane. Johansson et al. (2003) rejected tyrosinol for protein purification because "results clearly proved that the aromatic anion-exchangers have too strong secondary interactions to be practically useful." Nevertheless, "aromatic amines resulted in higher breakthrough capacities compared to the best non-aromatic anion-exchangers." Tyrosinol had a 63% greater dynamic binding capacity than the average of the five best non-aromatic anion-exchange ligands, and 36 times greater than the Q ligand when tested in high-salt buffer (23 mS/cm). Tyrosinol was rejected by Johansson et al. because it exhibited low recovery of bound protein. The fundamental goals for a disposable, virus-trapping membrane, however, are different from and diametrically opposed to those in protein purification. In virus trapping (as contrasted to protein purification) the binding protein to the filter medium (especially mAb) must be minimized. In virus trapping, the binding of the virus to the filter medium is preferably irreversible because there is no need to recover the bound virus. In contrast, in protein binding, the binding phenomenon must necessarily be reversible or the desired protein cannot be eluted from the column.

Preventing mAb binding can be accomplished by increasing the pKa of the ligand so that the mAb and ligand are both charged positive during loading. This causes electrostatic charge repulsion of the mAb from the ligand (Boschetti 2002; Morrow 2004). The virus, in contrast, is either negatively charged or is neutral, and binds to the ligand. Tyrosinol, for example, meets these requirements. It has a pKa of 10.8, making it positively charged at neutral pH. Most therapeutic mAbs tend to have pI's between 8 and 10. This narrow pI range is because therapeutic mAbs tend to be human IgG1, or to a much lesser extent IgG4. Because the V regions of an antibody are a small percentage of the total molecule, charge is largely determined by isotype. Thus, mAbs are positively charged at neutral pH, which prevents their binding to anion exchange media (Curtis et al. 2003). Viruses, on the other hand, can have a variety of pI's and many have negative pI's.

The multi-modal ligands for use in the present invention are selected based on the above criteria and outcomes, i.e., it is salt tolerant due to strong secondary interactions and has a high pKa (e.g., >10) causing electrostatic charge repulsion of the mAb. The ligand is immobilized on a micro-porous membrane and the virus-containing fluid flows through the membrane while the virus is trapped by the ligand. The membrane containing the bound virus is disposable.

Figure 7:
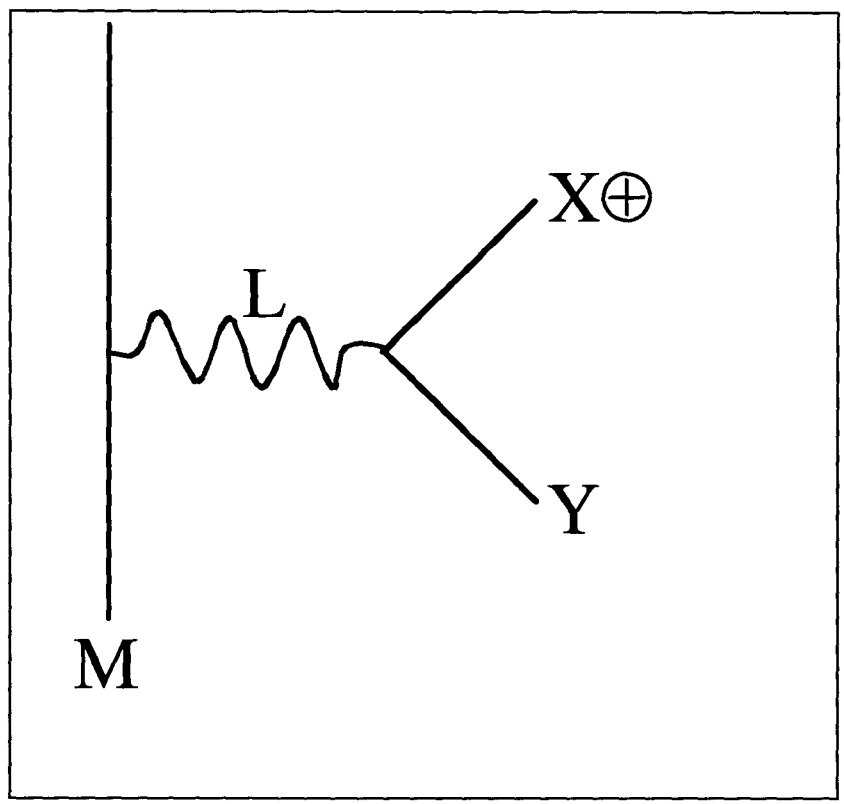
FIG. 7 is a schematic diagram of multi-modal ligand binding.

As shown in FIG. 7, the surface of the membrane (M) contains an immobilized moiety that has dual functionality. One of the functionalities (X) is charged positive to cause electrostatic charge repulsion of proteins such as monoclonal antibodies that are charged positive at neutral pH. The other functionality (Y) provides non-electrostatic secondary interactions between the immobilized ligand and the viruses. Both functionalities undergo only non-covalent interactions with the viruses and proteins. The moiety is immobilized to the membrane by a linker molecule (L) that by itself may augment one or both of these functionalities.

For the moiety $X\oplus$, the desired positive charge at neutral pH can be achieved by an amine having a pKa of 7 or greater, preferably a pKa of 10 or greater. Primary ($RNH_2$), secondary ($R_2NH$), tertiary ($R_3N$), and quaternary amines ($R_4N^+$) are examples.

For the moiety Y, the desired secondary interactions can come from non-covalent interactions e.g., Lewis acid-base pairs, hydrogen bonding, hydrophobic interaction, dipole-dipole attraction, induction effects, and dispersion forces. For example, hydrogen-bonding interactions originate from strong dipole-dipole interactions in which a hydrogen atom serves as a bridge between two electronegative atoms, typically F, O, or N. Amides ($RC=ONRH$) are an example because the hydrogen that is covalently bound to the N atom can be shared with the O atom on the acyl group from another amide. Hydrophobic interactions can originate from non-polar groups such as alkyl moieties (e.g., methyl, ethyl, propyl, butyl, pentyl, hexyl, heptyl, octyl, isopropyl, isobutyl, and others) and aryl moieties (e.g., phenyl).

For the moiety L, a chain of atoms or molecular subunits can be used to covalently link the ligand to the membrane. A linker molecule may comprise an alkyl chain of from 1-20 carbon atoms, a carbohydrate chain of from 1-15 saccharide groups, a dextran chain of from 1-15 saccharide groups, an amino acids chain of from 1-25 amino acids, glutaraldehyde, polyethylene glycol, diglycidyl ether, and other linker chemistries known in the art (Hermanson G T, Krishna Mallia A, and Smith P K, Immobilized Affinity Ligand Techniques, Academic Press, San Diego, 1992.)

The membrane may be any microporous membrane material including, but not limited to, cellulose, regenerated cellulose, cellulose diactetate and triacetate, cellulose nitrate, polyethylene, polypropylene, polyethersulfone, polyinylidene difluoride, polymethylmethacrylate, and polycarbonate. The membrane pore size desired is from 0.1 to 10 µm, and a pore size of 0.5 to 1.5 µm is most desired. A membrane with a high surface area for the internal pore structure is desired, which typically corresponds to fine pore sizes. However, if the pore size is too small, then the membrane tends to plug with fine particulates present in the feed solution. The pore surface chemistry may be modified to include polymer coatings or brushes to increase capacity over the base material of the membrane itself. In this case, the ligand chemistry described above would be applied to the polymer coating or brushes.

One embodiment of the present invention is to attach separately, but on the same membrane, the two ligand functionalities shown in FIG. 7. That is, ligand X⊕ and Y could be attached separately at sites adjacent to each other on the membrane surface via separate linker molecules L. The membrane then has the two desired functionalities: (1) salt tolerance due to strong non-electrostatic secondary interactions from ligand Y, and (2) electrostatic charge repulsion of proteins such as monoclonal antibodies due to the like charge from ligand X⊕.

A broader impact of the invention disclosed herein is to affect regulatory policy regarding biopharmaceutical manufacture. In short, by applying chemical engineering principles to regulatory issues of prime concern to state and federal regulators, the results generated can guide public- and health-policy decision-making. A potential major outcome is regulatory relief for academic centers and small biotechnology firms that are developing therapeutic mAb products. By establishing bracketed generic conditions for virus removal by membrane adsorbers, developers of new mAbs will be able to cite project results in lieu of performing costly and time-consuming validation studies. Resources will be freed for more fruitful purposes, accelerating availability of therapeutic mAbs to consumers.

EXAMPLES

The following examples are included solely to provide a more complete description of the invention disclosed and claimed herein. The examples do not limit the scope of the invention in any fashion.

Example 1

A long-standing and unresolved problem exists in the field of viral clearance: conventional adsorptive membrane products for viral clearance cannot remove neutral viruses from feed solutions having even moderate salt concentrations. Salt tolerance is a critical factor in designing robust viral clearance technologies because many process solutions used in the fabrication of biopharmaceutical products must contain salt to minimize product aggregation.

Figure 8:
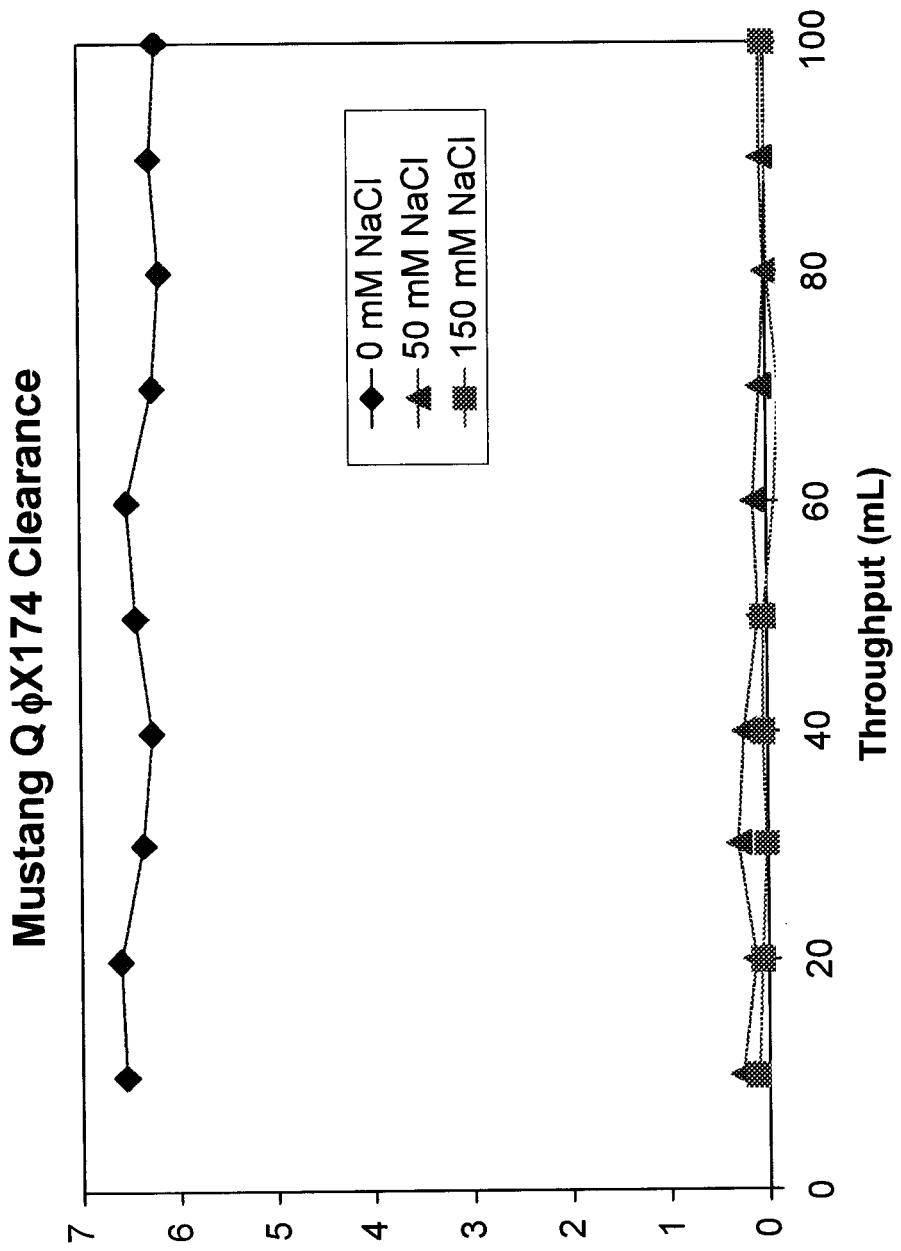
FIG. 8 is a graph depicting the log reduction value (Y-axis) of "MUSTANG"® Q-brand membrane filters as a function of throughput (X-axis) and salt concentration (♦=0 mM NaCl; ▲=50 mM NaCl; ■=150 mM NaCl). "MUSTANG" is a registered trademark of the Pall Corporation, East Hills, N.Y. See Example 1 for details.

Conventional adsorptive membrane products utilize a quaternary amine ligand for binding viruses. The "MUSTANG"® Q-brand product is a good example of a conventional filtration membrane that will very readily remove neutral viruses in solutions that have very small salt concentrations. By way of illustration, "MUSTANG"® Q-brand membrane will remove a neutral virus ($\phi$X174, pI=6.6) in a feed solution at pH 7.5, to a seven (7) Log Reduction Value (LRV), but only if the solution does not contain any added salt (NaCl). See FIG. 8 (-♦-). But performing the same separation, using the same feed solution that contains 50 mM NaCl drops the LRV capacity of the membrane to essentially zero. See FIG. 8 (-▲-). The same effect is seen at 150 mM NaCl. See FIG. 8 (-■-). In short, at low salt concentrations the virus passes freely through the "MUSTANG"® Q-brand adsorptive membrane into the product. Similar results have been shown by others. For example, when the "MUSTANG"® Q-brand adsorptive ligand was immobilized to a polyvinylidene diflouride (PVDF) membrane from Millipore, viral clearance of $\phi$X174 dropped from 6 LRV to less than 1 LRV when salt concentration was increased from 0 to 50 mM salt (Phillips & Lutz 2003). The significance of these results is that salt concentrations in the 50 mM to 150 mM range are not uncommon in the biopharmaceutical processing industry.

In these examples, the neutral virus ($\phi$X174 is used because is one of five model non-pathogenic bacteriophage viruses commonly used in filtration studies to represent the gamut of physical properties of potential adventitious viruses of danger to humans (e.g., size, pI, presence or absence of a membrane). In short, the $\phi$X174 virus is an art-recognized virus for modeling viral clearance of dangerous pathogens.

The current viral safety assurance strategy for biopharmaceuticals should preclude the presence of viruses in the feed solution. Careful control of cell lines and raw materials should also prevent introducing virus into the manufacturing process. See, for example, the official document titled "Guidance for Industry: Q5A—Viral Safety Evaluation of Biotechnology Products Derived from Cell lines of Human or Animal Origin," published September 1998 under the aegis of the International Conference on Harmonisation of Technical Requirements for Registration of Pharmaceuticals for Human Use (ICH). (This document is widely referenced in the industry as "ICH Q5A.") However, despite best practices throughout the manufacturing process, viral contaminations in bioprocessing are essentially stochastic events that can arise at any point in the process (for example, from contaminated raw materials to contaminated packaging). Thus, it is impossible to predict with any accuracy which virus could be next introduced into a manufacturing process. Therefore, a manufacturer must be prepared to remove all viruses, even neutral viruses.

Example 2

To solve the problem of salt intolerance explained in Example 1, eight (8) ligands were examined (Table 2). These ligands were evaluated using two different function tests. In the first function test, bovine serum albumin (BSA) in 20 mM piperazine, pH 6.0, with and without added NaCl, was incubated with a functionalized regenerated cellulose membrane. Bound BSA was then measured using the bicinchoninic acid (BCA) colorimetric method. Function test 1 measured the static protein binding capacity of the membranes under conditions where the pH was close to the isoelectric point of the protein (pI of BSA=5.1). In this function test, the protein had only a weak charge and was sensitive to added salt. This first function test was designed to mimic the binding of a neutral virus where the charge is weak.

Function test 2 measured the LRV for the neutral virus φX174 using the functionalized membranes in flow mode with TE buffer (10 mM Tris, 1 mM EDTA, pH 7.5) with and without added NaCl. Each ligand was immobilized onto regenerated cellulose membranes having 0.45 μm pore diameter using allyl glycidyl ether. The allylated membrane was then brominated. Lastly the ligand was coupled to the membrane via the primary amine on the ligand. The results are shown in Table 2.

TABLE 2

| Ligand | Structure | NaCl (mM) | BSA Static Capacity (mg/m$^2$) | φX174 LRV |
|---|---|---|---|---|
| 2-aminoethyltrimethylammonium chloride (AETMA) | 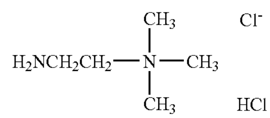 | 0 | 551 | 6.6 |
| | | 50 | 42 | 0.1 |
| | | 150 | 10 | 0.1 |
| Tyrosinol (TYR) | 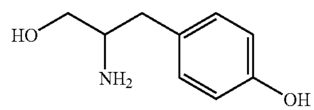 [SMILES: NC(CO)Cc1ccc(O)cc1] | 0 | 638 | 6.4 |
| | | 50 | 284 | 2.7 |
| | | 150 | 137 | 0.9 |
| Tryptophanol (TRP) | 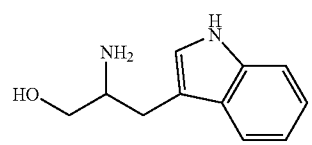 [SMILES: NC(CO)Cc1c[nH]c2ccccc12] | 0 | 668 | 5.4 |
| | | 50 | 297 | 1.1 |
| | | 150 | 131 | 1.0 |
| Octopamine (OCT) | 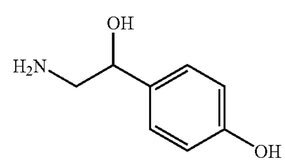 [SMILES: NCC(O)c1ccc(O)cc1] | 0 | 280 | 5.4 |
| | | 50 | 290 | 1.1 |
| | | 150 | 250 | 0.7 |
| 2-aminobenzimidazole (ABI) | 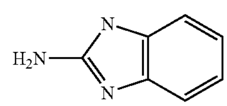 | 0 | 414 | 5.4 |
| | | 50 | 204 | 1.8 |
| | | 150 | 108 | 1.0 |
| Phenylalaninol (PHA) | 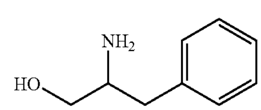 [SMILES: NC(CO)Cc1ccccc1] | 0 | 330 | 2.8 |
| | | 50 | 46 | 0.1 |
| | | 150 | 10 | 0.0 |
| 1,3-diamino-2-hydroxypropane (DHP) | 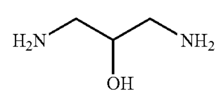 | 0 | 946 | 5.4 |
| | | 50 | 392 | 2.1 |
| | | 150 | 85 | 0.1 |
| tris(2-aminoethyl)amine (TAEA) | 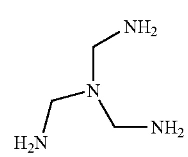 | 0 | 929 | 7.6 |
| | | 50 | 402 | 5.8 |
| | | 150 | 136 | 5.1 |
| Agmatine (AGM | 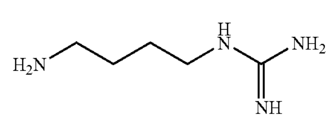 | 0 | 1000 | 5.5 |
| | | 50 | 319 | 5.5 |
| | | 150 | 116 | 5.9 |
| Blank | | 0 | 19 | 0.1 |
| | | 50 | 26 | 0.1 |
| | | 150 | 19 | 0.1 |

The first ligand in Table 2 is the traditional strong anion-exchange moiety [2-aminoethyltrimethylammonium chloride, AETMA] used in existing products such as the "MUSTANG"® Q-brand membrane. As expected from Example 1, AETMA was not salt tolerant. It rapidly lost capacity for the virus (φX174) even at moderate salt concentration.

The other ligands are examples of salt-tolerant moieties taken from the work of Johansson et al. (2003) that targeted protein purification (as contrasted to viral clearance) using agarose chromatography beads. The Johansson et al. group developed salt tolerant ligands for purifying proteins using regenerable and reusable agarose beads. The goal of the present work, however, is distinct because the problem to be solved is viral clearance in the context of a manufacturing process. The process needs to be easy, reproducible, and validatable. Thus, in the present invention, it is preferred to use disposable membranes. It is also preferred that the binding interaction between the virus and the membrane is irreversible. Lastly, in the present invention, the virus is cleared from the process solution selectively; the membrane does not bind the therapeutic protein. In other words, in the present invention, virus is trapped selectively and irreversibly onto the membrane, while the therapeutic protein target is not adsorbed to the membrane. The spent membrane is then disposed to avoid contamination of subsequent batches of the therapeutic protein product. That is, rather than use a positively-charged ligand to bind the therapeutic protein, as in Johansson et al., the present invention utilizes a diametrically opposed approach: the positive charge on the ligand is used to repel the positively charged therapeutic protein, and simultaneously bind the negatively charged virus, thereby removing it from the processing stream.

Figure 9:
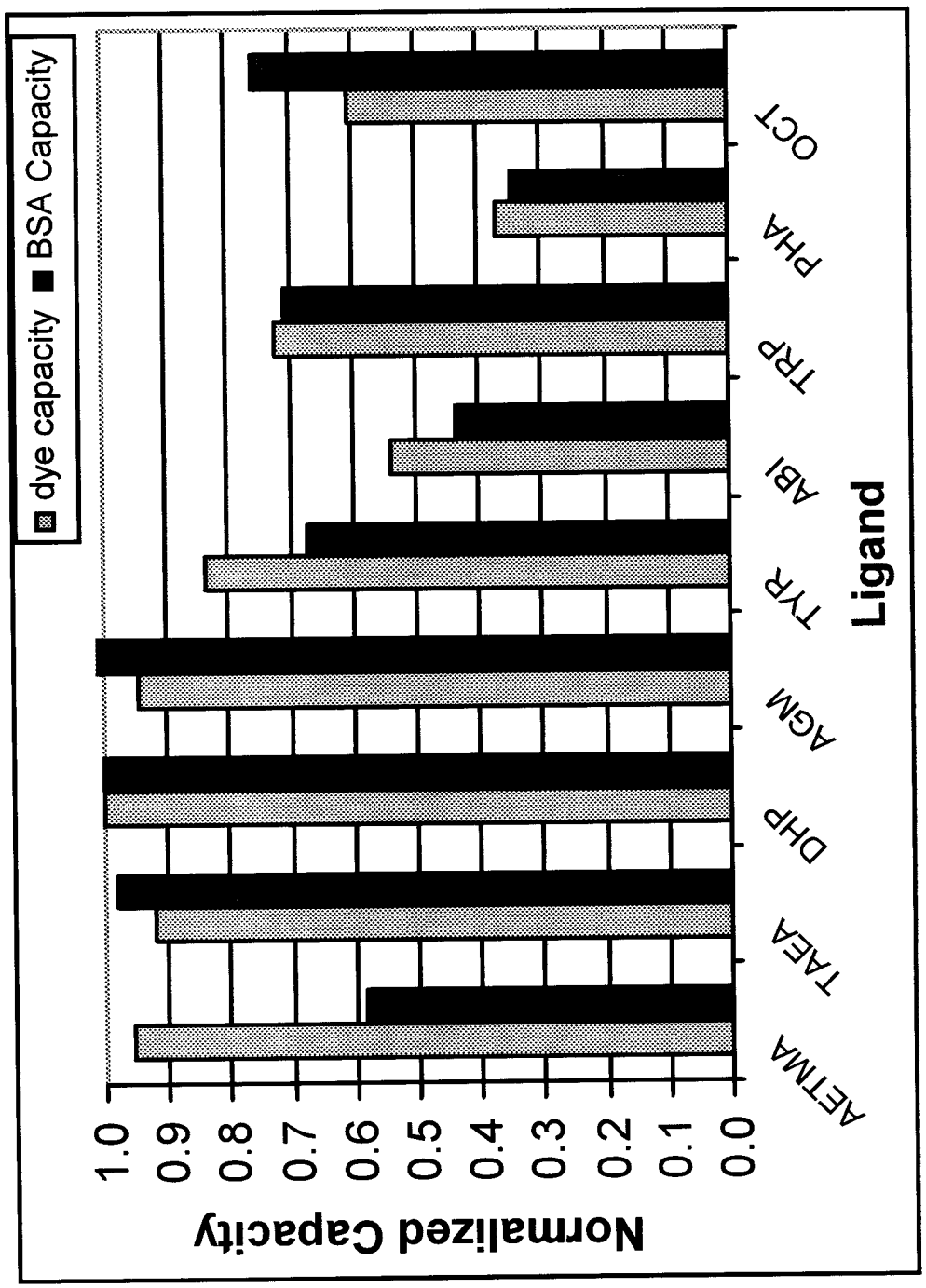
FIG. 9 is a histogram depicting the capacity of each ligand listed in Table 2 to bind an anionic dye and a negatively-charged protein (bovine serum albumin, BSA). See Example 2 for details.

As seen in FIG. 9, the capacity of each ligand to bind an anionic dye correlated well with the capacity of each ligand to bind a negatively-charged protein (BSA). However, viral clearance for each ligand was not as well predicted by the dye capacity or the protein capacity (Table 2). In addition, salt tolerance of the protein binding capacity was not correlated well with salt tolerance for viral clearance. In short, the results shown in FIG. 9 are relevant because they demonstrate that salt-tolerant viral binding characteristics of a membrane are not predictable from the protein-binding capacity of the same membrane.

For example, the non-aromatic ligands TAEA, DHP, and AGM all had similar capacities for the dye and for BSA. See FIG. 9. But viral clearance for TAEA was much greater than for DHP or AGM (see Table 2). Moreover, salt tolerance of the BSA capacity was similar for TAEA, DHP, and AGM, but salt tolerance of viral clearance was much less for DHP than for TAEA or AGM. For the aromatic ligands, salt tolerance of the BSA capacity was similar for TYR, TRP, and ABI, and highest for OCT (see Table 2). In contrast, salt tolerance of viral clearance was highest for TYR, and similar for OCT, TRP, and ABI. Further still, OCT had a higher salt tolerance for BSA than AGM or TAEA, yet OCT gave a substantially lower salt tolerance for viral clearance than AGM or TAEA. The ability to bind a neutral protein and an anionic dye was not predictive for the ability to bind a neutral virus.

The aromatic ligand TYR is a good example a ligand rejected for use in protein purification because binding of protein was too strong. The TYR ligand, however, is very well suited for use in viral clearance. As shown in Table 2, in the absence of added salt, TYR exhibited a LRV of 6.4 for virus. Clearance dropped to 2.7 LRV in the presence of 50 mM salt, and 0.9 LRV in the presence of 150 mM salt. These results were superior to the AETMA, where clearance was negligible in the presence of salt (LRV 0.1). These results illustrate the point that the requirements for salt tolerant and disposable membranes for viral clearance are so different from the requirements for salt tolerant and reusable beads for protein purification that ligands rejected for the protein purification are desired and superior for viral clearance.

Example 3

In addition to salt-tolerant viral clearance, another advantage of the present invention is that basic proteins, such as monoclonal antibodies (mAbs) are not bound to the membrane. This is accomplished by increasing the pKa of the ligand so that the mAb and ligand are both positively-charged during loading. This causes an electrostatic charge repulsion of the mAb from the ligand, yet has no adverse effect on the ability of the membrane to bind virus. Most therapeutic mAbs have pI's between about 8 and about 10. This narrow pI range exists because therapeutic mAbs tend to be human IgG1, or to a much lesser extent IgG2 and IgG4. Because the V regions of an antibody are a small percentage of the total molecule, charge is determined largely by isotype. Thus, mAbs are generally charged positive at neutral pH, which prevents binding to anion exchange media (Curtis et al. 2003). Viruses, on the other hand, have a variety of lower pI's, and many are negatively charged at neutral pH.

Figure 10:
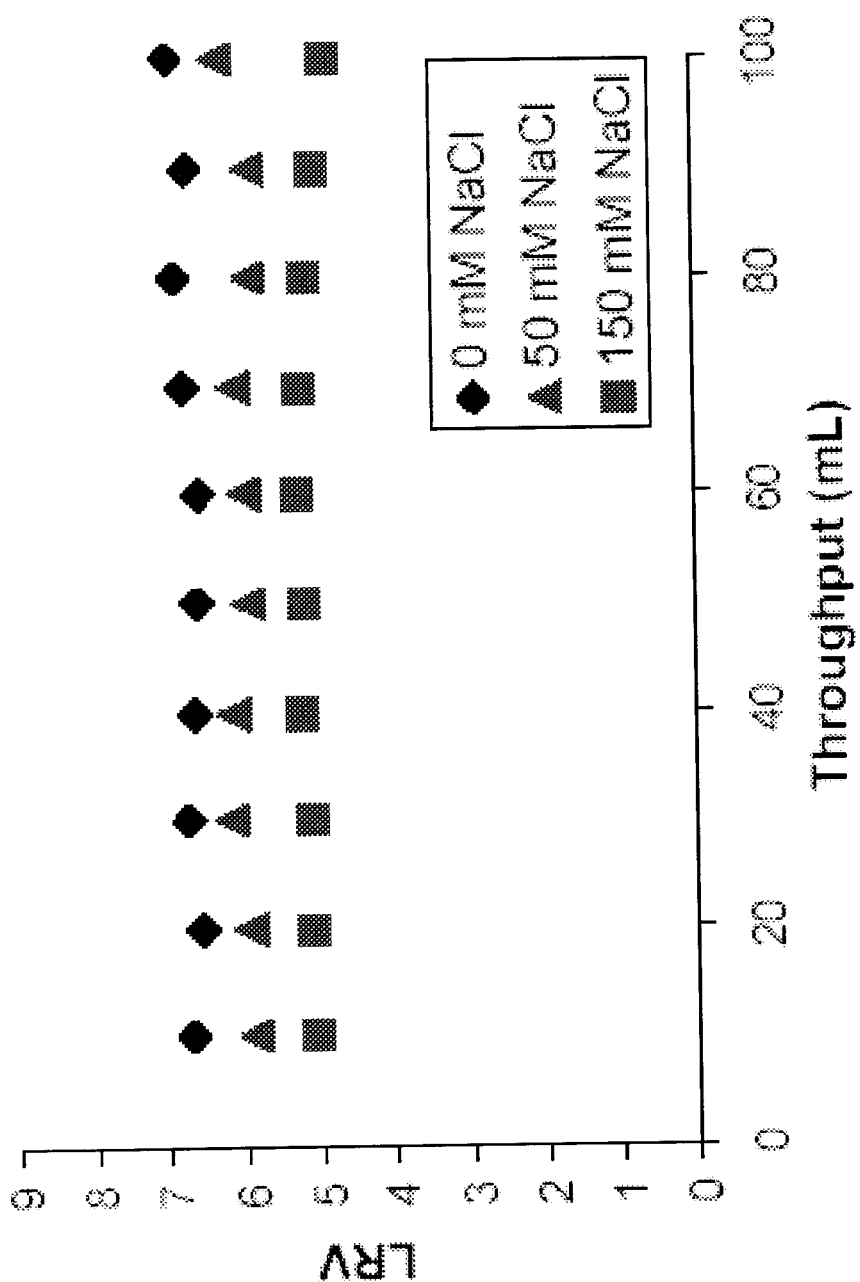
FIG. 10 is a graph depicting the performance of a virus-trapping membrane containing the immobilized ligand agmatine to remove a neutral virus (φX174) from a solution comprising a basic protein (0.5 g/L ribonuclease) and different concentrations of salt (♦=0 mM NaCl; ▲=50 mM NaCl; ■=150 mM NaCl).

AGM, for example, meets these requirements. It has a positive charge at neutral pH because the guanidine moiety has a pKa of 12.5. According to the methods of Example 2, a disposable, micro-porous, regenerated-cellulose virus-trapping membrane was fabricated containing the ligand AGM immobilized on the membrane. The basic protein ribonuclease A (pI~9.5) was used as a mAb surrogate. A feed solution comprising the neutral virus φX174 and 0.5 g/L of the basic protein ribonuclease A, both dissolved in TE buffer (10 mM Tris, 1 mM EDTA, pH 7.5), with and without added NaCl, was loaded into the membrane. The results are shown in FIG. 10. Viral clearance was not reduced by the presence of the basic protein. For example, compared to a viral clearance of 5.5 to 6.0 LRV without the basic protein and without and with added salt (Table 2), the viral clearance for AGM was not reduced at all after adding the basic protein (LRV≈6.0, FIG. 10). The significance of this example is two-fold: it demonstrates salt-tolerant virus trapping of the present invention and simultaneous repulsion of basic proteins by electrostatic charge repulsion.

BIBLIOGRAPHY

Anonymous. "Guidance on Viral Safety Evaluation of Biotechnology Products Derived from Cell Lines of Human or Animal Origin." Fed. Regist., 63, 51074-51084, 1998.

Anonymous. "Points to Consider in the Manufacture and Testing of Monoclonal Antibody Products for Human Use." Center For Biologics Evaluation and Research, Food and Drug Administration, U.S. Department of Health and Human Services, Rockville, Md., 1997.

Aranha-Creado, H., Brandwein, H. "Application of Bacteriophages as Surrogates for Mammalian Viruses: A Case for Use in Filter Validation Based on Precedents and Current Practices in Medical and Environmental Virology." PDA J. Pharm. Sci. Technol., 53, 75-82, 1999.

Barsoum, J., "Concentration of Recombinant Baculovirus by Cation-Exchange Chromatography." BioTechniques, 26, 834-840, 1999.

Benson, S. D., Bamford, J. K., Bamford, D. H., Burnett, R. M. 'Viral Evolution Revealed by Bacteriophage PRD 1 and Human Adenovirus Coat Protein Structures." Cell, 98, 825-833, 1999.

Bitzer, M., H. Yang, M. R. Etzel, "Analysis of Protein Purification Using Ion-Exchange Membranes," md Eng. Chem. Res., 38, 4044-4050 (1999).

Bitzer, M., "Mass Transfer Limitations Using Ion Exchange Membranes," bibl. Diplomarbeit Thesis, University of Stuttgart, Germany (1997).

Boschetti, E., "Antibody Separation by Hydrophobic Charge induction Chromatography." Trends Biotechnol., 20, 33 3-337, 2002.

Boulanger, P., Kroner-Lux, G., Moullier, P., Rolling, F., Salvetti, A., "A Versatile and Scalable Two-Step Ion-Exchange Chromatography Process for the Purification of Recombinant Adeno-AssociatedVirus Serotypes-2 and 5." Molecular Therapy, 6,678-686, 2002.

Brandt, S, Goffe R A, Kessler S B, O Connor J L. Membrane-based affinity technology for commercial scale separations. Bio/Technology 1988; 6:779-782.

Brorson, K., Krejci, S., Lee, K., Hamilton, E., Stein, K., Xu, Y. "Bracketed Generic Inactivation of Rodent Retroviruses by Low pH Treatment for Monoclonal Antibodies and Recombinant Proteins." Biotechnol. Bioeng., 82, 32 1-329, 2003.

Brough, H., Antoniou, C., Carter, J., Jakubik, J., Xu, Y., Lutz, H. "Performance of a Novel Viresolve NFR Virus Filter." Bioteclinol. Prog., 18, 782-795, 2002.

Brument, N., Morenweiser, R, Blouin, V., Toublane, E., Raimbaud, I., Cherel, Y., Foiliot, S., Gaden, F., Charcosset, C. Purification of proteins by membrane chromatography. J Chem Technol Biotechnol 1998; 71:95-110.

Coetzec, J. N., Lecaisas, G., Coetzee, W. F., Hedges, R W. "Properties of R Plasmid R772 and the Corresponding Pilus-Specit Ic Phage PR772." 3. Gen. Microbiol., 110, 263-273, 1979.

Curtis, S., Lee, K., Blank, G. S., Brorson, K., Xu, Y. "Generic/ Matrix Evaluation of 5V40 Clearance by Anion Exchange Chromatography in Now-Through Mode." Biotechnol. Bioeng., 84, 179-186, 2003.

Das, R C. "Progress and Prospects of Protein Therapeutics." American Biotechnology Laboratory, 10, 8-12, 2003.

Debelak, D., Fisher, 3., luliano, S., S-~sholtz, D., Sloane, D. L., and Atkinson, E. M., "Cation-Exchange High-Performance Liquid Chromatography of Recombinant Adeno-Associated Virus Type 2." 3. Chromatogr. A, 740, 195-202, 2000.

DePalma, A., "Introducing Innovations to Downstream Process." Genetic EngineeringNews, 23, 47-48, 2003.

Dowd, S. E.; Pillai, S. D.; Wang, S.; Corapeioglu, M. Y.; "Delineating the Specific Influence of Virus Isoelectric Point and Size on Virus Adsorption and Transport through Sandy Soils." Appl. Environ. Microbiol., 1998, 64(2), 405-4 10.

Eamshaw, W. C.; King, 3.; Eiserling, F. A.; "The Size of the Bacteriophage T4 Head in Solution with Comments about the Dimension of Virus Particles as Visualized by Electron Microscopy." J. Mol. Biol., 1978, 122, 247-253.

Endres, H. N., Johnson, J. A. C., Ross, C. A., Welp, J. K., "Evaluation of an Ion Exchange Membrane for Purification of Plasmid DNA." Biotechnol. Appl. Biochem., 37,259-266, 2003.

Etzel, M., "Layered Stacks," in Monolithic Materials: Preparation, Properties and Applications, F. Svec, T B. Tennikova and Z. Deyl (eds.), Ch 10, Elsevier Science, Amsterdam (2003).

Fischer, J., "Separation of Nanometer-Sized Biological Particles Using Membrane Chromatography: An Analysis of Adsorption Kinetics, M. S. Thesis, Univ. Wisconsin (2000).

Fischer, J., "Separation of Nanometer-Sized Biological Particles Using Membrane Chromatography: An Analysis of Adsorption Kinetics." M. S. Thesis, Univ. Wisconsin, 2000.

Fogler, H S. Elements of Chemical Reaction Engineering. 2d ed Englewood Cliffs, N.J.: Prentice-Hall, 1992.

Gerba, C. P. "Applied and Theoretical Aspects of Virus Adsorption to Surfaces." Adv. Appl. Microbiol., 30, 133-168, 1984.

Ghosh, R. Protein separation using membrane chromatography: opportunities and challenges. J Chromat A 2002; 952: 13-27.

Heister, N K, Venneulen T. Saturation performance of ion-exchange and adsorption columns. Chem Eng Prog 1952; 48:505-5 16.

Hermanson, G. T., Krishna Mallia, A., Smith, P. K. "Immobilized Affinity Ligand Techniques," Academic Press, San Diego, 1992.

Huyghe, B. G., Liu, X, Sutjipto, S., Sugarman, B. J., Horn, M., Shepard, H. M., Scandella, C. J., Shabram, P. "Purification of a Type S Recombinant Adeovirus Encoding Human p53 by Column Chromatograhy." Human Gene Therapy, 6, 1403-14 16, 1995.

Johansson, B. L, Belew, M., Eriksson, S., Glad, G., Lind, O., Maloisel, J. L, Norrman, N. "Preparation and Characterization of Prototypes for Multi-Modal Separation Media Aimed for Capture of Negatively Charged Biomolecules at High Salt Conditions." J. Chromat. A, 1016, 21-33, 2003.

Lin, S., Carroll, M., Iverson, R., Valera, C., Vennari, 3., Turco, K., Piper, R, Kiss, R., Lutz, H. "Development and Qualification of a Novel Virus Removal Filter for Cell Culture Applications." Biotechnol. Prog., 16,425-434, 2000.

Lundstr6m, I., "Models of Protein Adsorption on Solid Surfaces." Prog. Colloid Polym. Sci., 70, 76.82, 1985.

Lute, S., Aranha, H., Tremblay, D., Liang, D., Ackermann, H. W., Chu, B., Moineau, S., Brorson, K., "Virus-Retentive Filter Nomenclature: Characterization of the Coliphage PR772Recommended for Virus Filter Performance Testing." Appl. Environ. Microbiol., in press, 2004

Lyddiatt, A., O Sullivan D. A., "Biochemical Recovery and Purification of Gene Therapy Vectors." Curr. Opin. Biotechnol., 9, 177-185, 1998.

Millipore Technical Brief, Viresolve NF1 Filters Predictably Scale, TB 1O2OENOO, Bedford, Mass., 2002.

Morrow, KJi, "Antibody Technology Highlighted in Europe—Updates in Rational Design, Purification, and Manufacturing Presented at Meeting." Genetic Eng. News, 24, 52-56, 2004.

O'Leary, R'Feuerhelm, D., Peers, D., Xu, Y., Blank. (1.5. "Determining the Useful Lifetime of Chromatography Resins: Prospective Small-Scale Studies." BioPliarm., 14, 10-18, 2001.

Oshima, K. H., Evans-Strickfaden, T. T., Highsmith, A. K., Ades, E. W. "The Use of a Microporous Polyvinylidene Fluoride (PVDF) Membrane Filter to Separate Contaminating Viral Particles from Biologically Important Proteins:—" fliologicals, 24, 137-145, 1996.

Penrod, S. L., Olson, T. H., Grant, S. B., "Whole Particle Microelectrophoresis of Small Viruses and Colloids." 3. Colloid Interfacial Sci., 173, 521-523, 1995.

Phillips, M. W., Lutz, H. "Membrane Adsorber Technology for Trace Impurity Removal Applications." Abstr. Papers Am. Chem. Soc., 225: 116-Biot Part I, Mar. 25, 2003.

Phillips, M, Cormier J, Ferrence J, Dowd C, Kiss R, Lutz H, Carter 3. Performance of a membrane adsorber for trace impurity removal in biotechnology manufacturing. 3 Chromat A 2005; 1078:74-82.

Rao, C. S., "Mass Transfer in Protein Separations Using Ion Exchange Membranes," M. S. Thesis, Univ. Wisconsin (1998).

Roper, D K, Lightfoot E N. Separation of biomolecules using adsorptive membranes. J Chromat A 1995; 702:3-26.

Sarfert, F. T., M R. Et. zel, "Mass Transfer Limitations in Protein Separations Using Ion Exchange Membranes," J. Chromat. A, 764, 3-20 (1997).

Schnable, U., Groiss, F., Blaas, D., Kenndler, E., "Determination of the p1 of Human Rhinovirus Serotype 2 by Capillary Isoelectric Focusing." Anal. Chem., 68, 4300-4303, 1996.

Shabram, P. W., Giroux, D. D., Goudreau, A. M., Gregory, R J., Horn, M. T., Huyghe, B. G., Lin, X., Nunnally, M. H., Sugarman, B. J., Sutjipto, S., "Analytical Anion-Exchange HPLC of Recombinant Type-Adenoviral Paricles." Human Gene Therapy, 8, 453-465, 1997.

Sofer, G. "Nanoflltration-PDA Virus Filter Task Force Status Report." PDA/EMEA European Virus Safety Forum, Langen, Germany, 2003.

Soltys, P. J., MK Etzel, "Equilibrium Adsorption of LDL and Gold Immunoconjugates to Affinity Membranes Containing PEG Spacers," Biomaterials, 21, 37-48 (2000).

Soltys, P. J., M. R. Etzel, "In Vitro Characterization of a Membrane-Based Low-Density Lipoprotein Affinity Adsorption Device," Blood Purif, 16, 123-134 (1998).

Talbot, J., Tarjus, (1., Van Tassel, P. R, Viot, P. "From Car Parking to Protein Adsorption: An Overview of Sequential Adsorption Processes." Colloids Surfaces A: Physicochem. Eng. Aspects, 165,287-324, 2000.

Thömmes, J, Kula M R. Membrane chromatography an integrative concept in the downstream processing of proteins. Biotechnol Prog 1995; 11:357-367.

van Regenmortel, M., Fauquet, C., Bishop, D., Carstens, E., Estes, M., Lemon, S., Maniloff, 3., Mayo, M., MeGeoch, D., Pringle, C., Wickner, R "Virus Taxonomy, Classification and Nomenclature of Viruses." 7th Ed., Academic Press, San Diego, 2000.

Viera, C., H. Yang. M. R. Etzel, "Affinity Membranes: Competitive Binding of the Human IgG Subclasses to Immobilized Protein G," md Eng. Chem. Res., 39, 3356-3363 (2000).

Viera, C., J. Fischer, H. Yang, M. R. Etzel, "Purification of a Large Protein Using Ion Exchange Membranes," md Eng. Chem. Res., 41, 1597-1602 (2002).

Xu, Y., Brorson, K. "An Overview of Quantitative PCR Assays for Biologics Quality and Safety Evaluations. Developments in Biologicals." 113, 89-98, 2003.

Yang, H., M. R Etzel, "Evaluation of Three Kinetic Equations in Models of Protein Purification Using Ion-Exchange Membranes," Ind Eng. Chem. Res., 42, 890-896 (2003).

Yang, H., Bitzer, M., Etzel, M R. "Analysis of Protein Purification Using Ion-Exchange Membranes." hid. Eng. Chem. Res., 38, 4044-4050, 1999.

Yang, H., Viera, C., Fischer, J., Etzel, M. R, "Purification of a Large Protein Using Ion-Exchange Membranes." Ind. Eng. Chem. Res., 41, 1597-1602, 2002.

Ywnamoto, S, Miyagawa, E, "Retention Behavior of Very Large Biomolecules in Ion-Exchange Chromatography." I Chromatogr. A, 852, 25-30, 1999.

Zeng, X, Ruckenstein E. Membrane chromatography: preparation and applications to protein separation. Biotechnol Prog 1999; 15:1003-1019.

What is claimed is:

1. A disposable, virus-trapping membrane comprising:
a disposable, micro-porous filter membrane; and
a multi-modal anion-exchange ligand immobilized on the membrane, wherein the ligand is dimensioned and configured to:
  (a) bind neutral viruses;
  (b) have a pKa sufficiently high to repel basic proteins via electrostatic charge repulsion; and
  (c) yield a log-reduction value (LRV) of at least 1.0 for the neutral viruses disposed in a solution comprising 50 mM salt.

2. The virus-trapping membrane of claim 1, wherein the ligand has a positive charge at pH 7.

3. The virus-trapping membrane of claim 1, wherein the ligand has a pKa of at least 10.0.

4. The virus-trapping membrane of claim 1, wherein the filter membrane comprises a polymer substrate selected from the group consisting of polyvinylidene difluoride, polytetrafluorethylene, polyamides, polyamide-imides, polysulfones, polyethersulfones, and polyphenylsulfones.

5. The virus-trapping membrane of claim 1, wherein the ligand is dimensioned and configured to yield a log-reduction value (LRV) of at least 1.0 for neutral viruses disposed in a solution comprising 150 mM salt.

6. The virus-trapping membrane of claim 1, wherein the ligand is dimensioned and configured to yield a log-reduction value (LRV) of at least 5.0 for neutral viruses disposed in a solution comprising 50 mM salt.

7. The virus-trapping membrane of claim 1, wherein the ligand is dimensioned and configured to yield a log-reduction value (LRV) of at least 5.0 for neutral viruses disposed in a solution comprising 150 mM salt.

8. The virus-trapping membrane of claim 1, wherein the ligand is selected from the group consisting of tyrosinol, tryptophanol, octopamine, 2-aminobenzimidazole, 1,3-diamino-2-hydroxypropane, tris(2-aminoethyl)amine, and agmatine.

9. A disposable, virus-trapping membrane comprising:
a disposable, micro-porous filter membrane; and
a ligand immobilized on the membrane, wherein the ligand is selected from the group consisting of tyrosinol, tryptophanol, octopamine, 2-aminobenzimidazole, 1,3-diamino-2-hydroxypropane, tris(2-aminoethyl)amine, and agmatine, and further wherein the ligand:
  (a) binds neutral viruses;
  (b) is a multi-modal anion-exchange ligand;
  (c) has a pKa sufficiently high to repel basic proteins via electrostatic charge repulsion; and
  (d) yields a log-reduction value (LRV) of at least 1.0 for the neutral viruses disposed in a solution comprising 50 mM salt.

10. The virus-trapping membrane of claim 9, wherein the ligand is selected from the group consisting of tryptophanol, 2-aminobenzimidazole, tris(2-aminoethyl)amine, and agmatine, and further wherein the ligand is dimensioned and configured to yield a log-reduction value (LRV) of at least 1.0 for neutral viruses disposed in a solution comprising 150 mM salt.

11. The virus-trapping membrane of claim 9, wherein the ligand is selected from the group consisting of tris(2-aminoethyl)amine and agmatine, and further wherein the ligand is dimensioned and configured to yield a log-reduction value (LRV) of at least 5.0 for neutral viruses disposed in a solution comprising 50 mM salt.

12. The virus-trapping membrane of claim 9, wherein the ligand is selected from the group consisting of tris(2-aminoethyl)amine and agmatine, and further wherein the ligand is dimensioned and configured to yield a log-reduction value (LRV) of at least 5.0 for neutral viruses disposed in a solution comprising 150 mM salt.

13. A method of removing viruses from a solution suspected of containing viruses, the method comprising:
contacting a solution suspected of containing viruses with virus-trapping membrane comprising a disposable, micro-porous filter membrane and a multi-modal anion-exchange ligand immobilized on the membrane, wherein the ligand is dimensioned and configured to bind neutral viruses, has a pKa sufficiently high to repel basic proteins present in the solution via electrostatic charge repulsion, and yields a log-reduction value (LRV) of at least 1.0 for the neutral viruses disposed in a solution comprising 50 mM salt.

14. The method of claim 13, wherein the solution is contacted with the virus-trapping membrane for a time sufficient to yield a log-reduction value (LRV) of at least 1.0 for neutral viruses disposed in the solution when the solution comprises from 0 to about 50 mM salt.

15. The method of claim 13, wherein the solution is contacted with the virus-trapping membrane for a time sufficient to yield a log-reduction value (LRV) of at least 1.0 for neutral viruses disposed in the solution when the solution comprises from 0 to about 150 mM salt.

16. The method of claim 13, wherein the solution is contacted with the virus-trapping membrane for a time sufficient to yield a log-reduction value (LRV) of at least 5.0 for neutral viruses disposed in the solution when the solution comprises from 0 to about 50 mM salt.

17. The method of claim 13, wherein the solution is contacted with the virus-trapping membrane for a time sufficient to yield a log-reduction value (LRV) of at least 5.0 for neutral viruses disposed in the solution when the solution comprises from 0 to about 150 mM salt.

18. The method of claim 13, wherein the solution is contacted with a disposable, micro-porous filter membrane comprising polyvinylidene difluoride; and the ligand immobilized on the membrane is selected from the group consisting of tyrosinol, tryptophanol, octopamine, 2-aminobenzimidazole, 1,3-diamino-2-hydroxypropane, tris(2-aminoethyl)amine, and agmatine.

19. The method of claim 18, wherein the ligand immobilized on the membrane is selected from the group consisting of tris(2-aminoethyl)amine and agmatine.

20. A disposable, virus-trapping membrane comprising:
a disposable, micro-porous filter membrane;
a multi-modal exchange ligand immobilized on the membrane, wherein the ligand is selected from the group consisting of tryptophanol, 2-aminobenzimidazole, tris(2-aminoethyl)amine, and agmatine, and further wherein the ligand is dimensioned and configured to:
(a) bind neutral viruses;
(b) have a pKa sufficiently high to repel basic proteins via electrostatic charge repulsion; and
(c) yield a log-reduction value (LRV) of at least 1.0 for the neutral viruses disposed in a solution comprising 150 mM salt.

21. The virus-trapping membrane of claim 20, wherein the ligand is dimensioned and configured to yield a log-reduction value (LRV) of at least 5.0 for the neutral viruses disposed in a solution comprising 150 mM salt.

22. The virus-trapping membrane of claim 20, wherein the ligand is selected from the group consisting of tris(2-aminoethyl)amine and agmatine, and is dimensioned and configured to yield a log-reduction value (LRV) of at least 5.0 for the neutral viruses disposed in a solution comprising 150 mM salt.

* * * * *